United States Patent [19]

Fulton et al.

[11] Patent Number: 5,266,205
[45] Date of Patent: Nov. 30, 1993

[54] SUPERCRITICAL FLUID REVERSE MICELLE SEPARATION

[75] Inventors: John L. Fulton; Richard D. Smith, both of Richland, Wash.

[73] Assignee: Battelle Memorial Institute, Richland, Wash.

[21] Appl. No.: 907,177

[22] Filed: Jul. 1, 1992

Related U.S. Application Data

[60] Division of Ser. No. 559,396, Jul. 25, 1990, Pat. No. 5,158,704, which is a continuation of Ser. No. 152,256, Feb. 4, 1988, abandoned.

[51] Int. Cl.$^5$ .............................................. B01D 15/00
[52] U.S. Cl. .................................... 210/639; 210/656; 210/659; 530/413; 530/417
[58] Field of Search ............... 210/639, 638, 635, 656, 210/659, 643, 634; 252/309; 530/413, 417, 38.5; 526/207

[56] References Cited

U.S. PATENT DOCUMENTS

| | | | |
|---|---|---|---|
| 4,797,474 | 1/1989 | Patroni et al. | 530/417 |
| 4,933,404 | 6/1990 | Beckman et al. | 526/207 |
| 5,135,657 | 8/1992 | Zavitsanos | 210/656 |
| 5,158,704 | 10/1992 | Fulton et al. | 252/309 |

OTHER PUBLICATIONS

R. W. Gale, J. L. Fulton & R. D. Smith "Reverse Micelle Supercritical Fluid Chromatography" *Anal. Chem.* 1987, 59, 77–79.

Goklen E. Kent and Hatton Alan T. "Liquid–Liquid Extraction of Low Molecular-Weight Proteins by Selective Solubilization in Reversed Micelles". S. S. & Technology, Marcel Dekker; New York, 1987, pp. 831–841.

Micelles, Physical Chemistry of Surfactant Association Physics Reports 52, No. 1 (1979) Jan. 1986 pp. 3–7.

J. B. Evans and D. F. Evans "A Comparison of Surfactant Counterion Effects in Water and Formamide" A.C.S. 1987 pp. 4–5.

R. W. Gale, J. L. Fulton and R. D. Smith "Organized Molecular Assemblies in the Gas Phase: Reverse Micelles and Microemulsions in Supercritical Fluids" *J.A.C.S.*, 109, 920 (1987).

R. D. Smith, J. L. Fulton and H. K. Jones "Reverse Micelle Supercritical Fluid Separations", *Separation Science Technology*, vol. 23, Oct., 1988.

(List continued on next page.)

*Primary Examiner*—Robert A. Dawson
*Assistant Examiner*—Ana M. Fortuna
*Attorney, Agent, or Firm*—Marger, Johnson, McCollom & Stolowitz

[57] ABSTRACT

A method of separating solute material from a polar fluid in a first polar fluid phase is provided. The method comprises combining a polar fluid, a second fluid that is a gas at standard temperature and pressure and has a critical density, and a surfactant. The solute material is dissolved in the polar fluid to define the first polar fluid phase. The combined polar and second fluids, surfactant, and solute material dissolved in the polar fluid is maintained under near critical or supercritical temperature and pressure conditions such that the density of the second fluid exceeds the critical density thereof. In this way, a reverse micelle system defining a reverse micelle solvent is formed which comprises a continuous phase in the second fluid and a plurality of reverse micelles dispersed in the continuous phase. The solute material is dissolved in the polar fluid and is in chemical equilibrium with the reverse micelles. The first polar fluid phase and the continuous phase are immiscible. The reverse micelles each comprise a dynamic aggregate of surfactant molecules surrounding a core of the polar fluid. The reverse micelle solvent has a polar fluid-to-surfactant molar ratio W, which can vary over a range having a maximum ratio $W_o$ that determines the maximum size of the reverse micelles. The maximum ratio $W_o$ of the reverse micelle solvent is then varied, and the solute material from the first polar fluid phase is transported into the reverse micelles in the continuous phase at an extraction efficiency determined by the critical or supercritical conditions.

30 Claims, 18 Drawing Sheets

OTHER PUBLICATIONS

K. S. Schange, et al., "Solubilization in Surfactant Medica: Use of an Isomerizable Solute Probe to Determine Microheterogeneity in Microemulsions" J.A.C.S. (1983) 105 pp. 6734–6735.

Neogi, P., "Oil Recovery and Microemulsions," *Microemulsions: Structure and Dynamics*; Friberg, S. E.; Bothorel, P. Eds.; CRC Press: Boca Raton, 1987, pp. 197–210.

Langevin, D., "Technological Relevance of Microemulsions and Reverse Micelles In Apolar Media," *Reverse Micelles*; Luisi, P. L., Straub, B. E., Eds.; Plenum Press: New York, 1984; pp. 287–303.

Luisi, P. L., "Angew. Chem. Int. Engl.," 1985, 24, 439–450.

Leong, Y. S.; Candau, F., "Inverse Microemulsion Polymerization," Journal of Phys. Chem., 1982, 86, 2269–2271.

Luisi, P. L., Meier, P., Imre, V. E., Pande, A., "Enzymes and Nucleic Acids Solubilized in Hydrocarbon Solvents with the Help of Reverse Micells," *Reverse Micelles*; Luisi, P. L.; Straub, B. E., Eds.; Plenum Press: New York, 1984, pp. 323–337.

Hernandez-Torres, M. A.; Landy, J. S.; Dorsey, J. G., "Reversed Micellar Mobile Phases for Normal-Phase Chromatography," Anal. CXhem., 1986, 58, 744–747.

Göklen, K. E.; Hatton, T. A.; "Protein Extraction Using Reverse Micelles," Biotechnol. Prog., 1985, 1, 69–74.

Eicke, H. F.; Kubik, R.; Hasse, R.; Zschokke, I., "The Water-In-Oil Microemulsion Phenomenon: Its Understanding and Predictability from Basic Concepts," *Surfactants in Solution*; Mittal, K. L., Lindman, B.; Eds.; Plenum Press: New York, 1984, pp. 1533–1549.

Zulauf, M.; Eicke, H. F., "Inverted Micelles and Microemulsions in the Ternary System $H_2O$/Aerosol-OT/Isooctane as Studied by Photon Correlation Spectroscopy," *J. Phys. Chem.*, 1979, 83, 480–486.

Kotlarchyk, M.; Huang, J. S.; Chen, S. H., "Structure of AOT Reversed Micelles Determined by Small-Angle Neutron Scattering," *J. Phys. Chem.*, 1985, 89, 4382–4386.

Wong, J. M.; Johnston, K. P., "Solubilization of Biomolecules in Carbon Dioxide Based Supercritical Fluids," *Biotechnol. Prog.*, 1986, vol. 2, No. 1, 29–39.

Schneider, G. M., "Physicochemical Principles of Extraction with Supercritical Gases," Angew. Chem. Int. Ed. Engl., 1978, 17, 716–727.

Evans, D. F.; Mitchell, D. J.; Ninham, B. W., "Oil, Water, and Surfactant: Properties and Conjectured Structure of Simple Microemulsions," *J. Phys. Chem.*, 1986, 90, 2817–2825.

Nagy, J. B.; Gourgue, A.; DeRouane, E. G., "Preparation of Monodispersed Nickel Boride Catalysts Using Reversed Micellar Systems," *Preparation of Catalysts III*, 1983, pp. 193–202.

El Seoud, O.A., Chinelatto, A. M. Shimizu, M. R., "Acid-Base Indicator Equilibria in the Presence of Aerosol-OT Aggregates in Heptane," *J. Colloid Interface Sci.*, 1982, 88, 420–427.

Assih, T., Delord, P., Larché, F. C., "Existence of Transparent Unstable Solutions in Three and Four Components Surfactant Systems," *Surfactants In Solution*, Mittal, K. L., Lindman, B., Eds.; Plenum Press: New York, 1984; vol. 3, pp. 1821–1828.

Rizzo, V. J., "Hydrophilic Molecules Solubilized in Water-In-Oil Microemulsions: Distribution of Species in a Chemical Equilibrium," *Colloid Interface Sci.*, 1986, vol. 110, 110–113.

Ramesh, V.; Labes, M. M., "Control of Reaction Kinetics by Manipulation of Micellar Size and Shape," J. Am. Chem. Soc., 1986, 108, 4643–4644.

Leser, M. E.; Weis, G.; Luisi, P. L.; Maestro, M., "Application of Reverse Micelles for the Extraction of Proteins," Biochem. Biophys. Acta, 1986, 235, 629–635.

Cline Love, L. J.; Habarta, J. G.; Dorsey, J. G., "The Micelle-Analytical Chemistry Interface," Anal. Chem., 1984, 56, 1132A–1148A.

Magid, L. J.; Kon-no, K.; Martin, C. A., "Binding of Phenols to Inverted Micelles and Microemulsion Aggregates," *J. Am. Chem. Soc.*, 1981, 85, 1434–1439.

Candau, F.; Leong, Y. S., "Kinetic Study . . . In Inverse Microemulsion," *Journal of Polymer Science*: Polymer Chem. Ed., vol. 23, 193–214 (1985).

Pileni, M. P., Zemb, T., Petit, C., "Solubilization by Reverse Micelles: Vol. Solute Localization and Structure Perturbation," *Chem. Phys. Lett.*, 1985, vol. 118, 414–420.

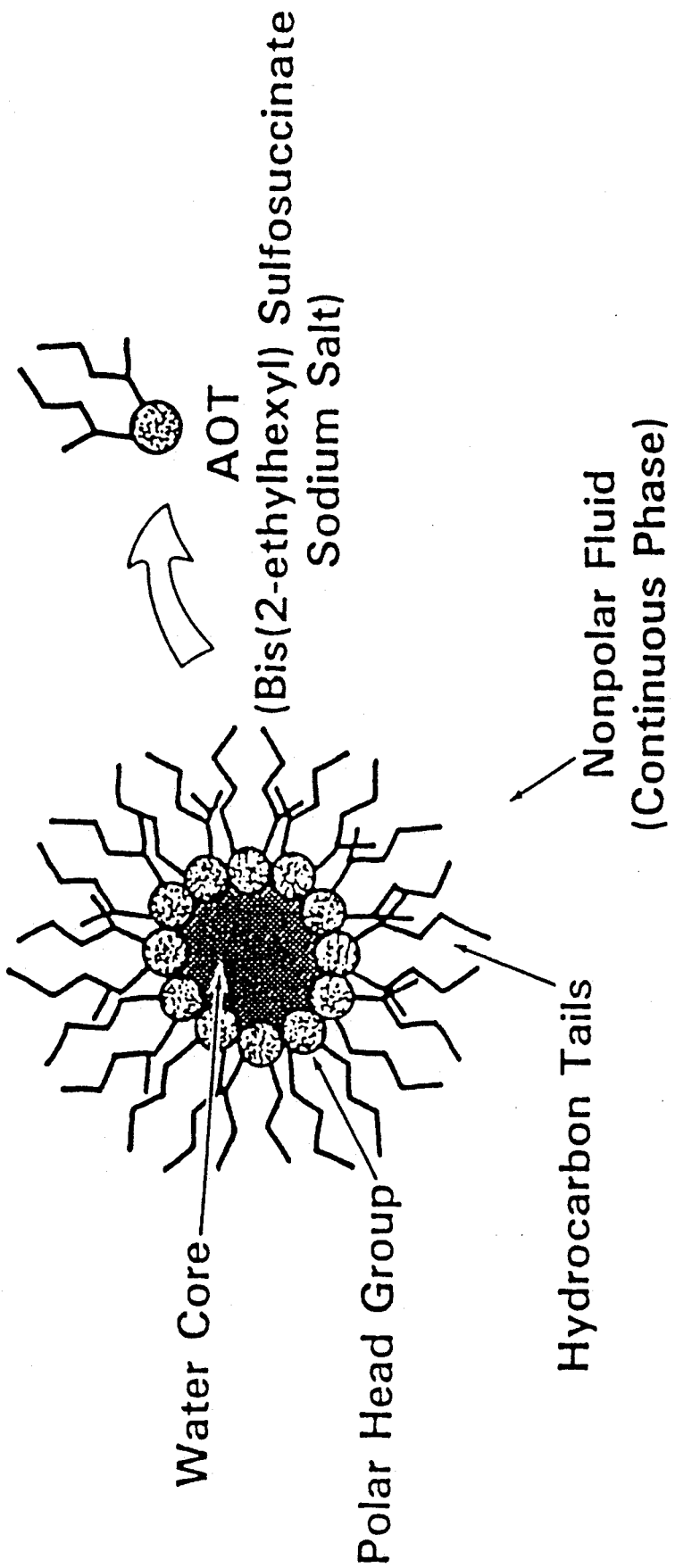
FIG. 1 Reverse Micelle

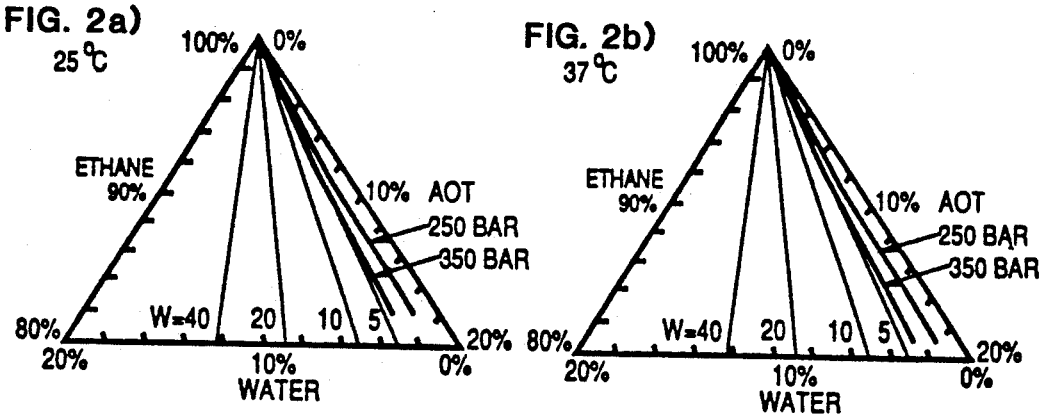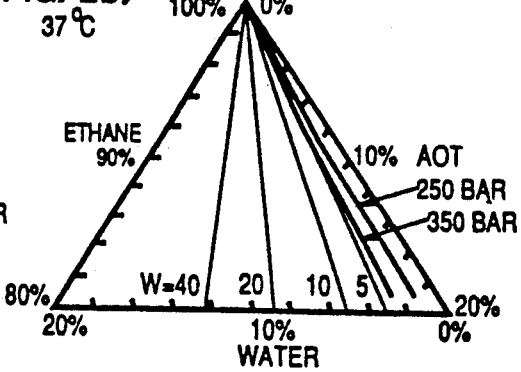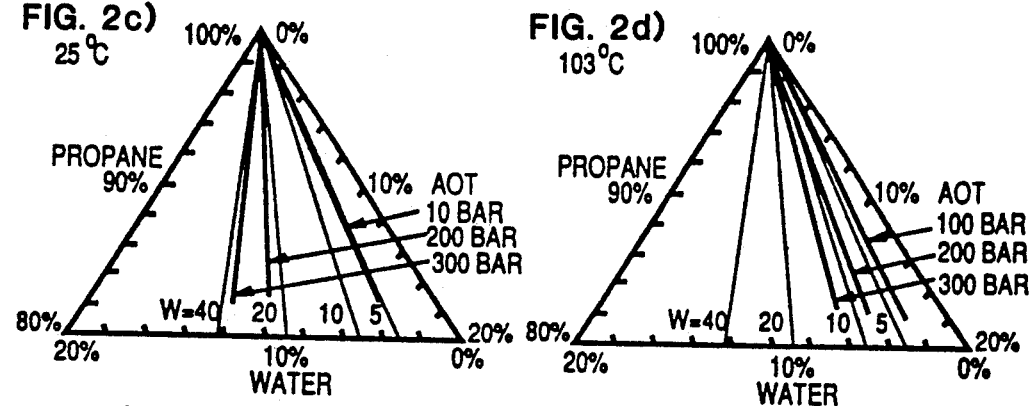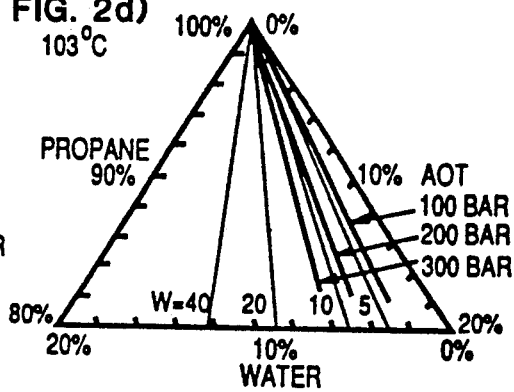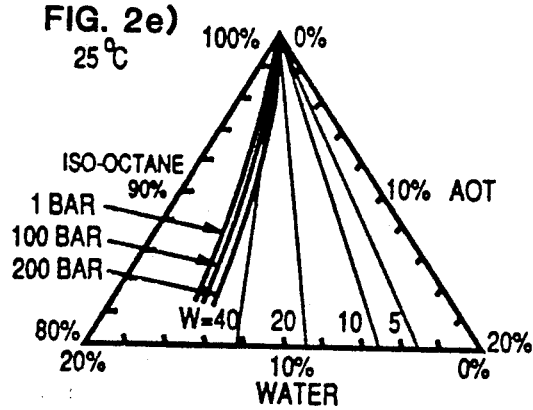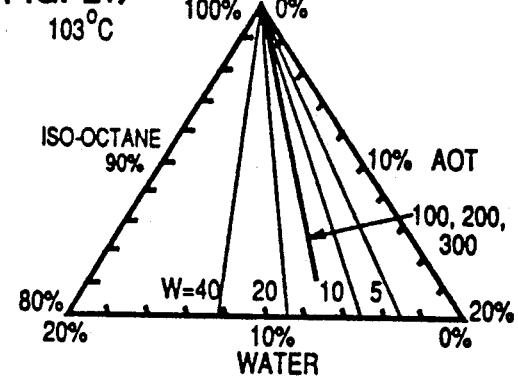

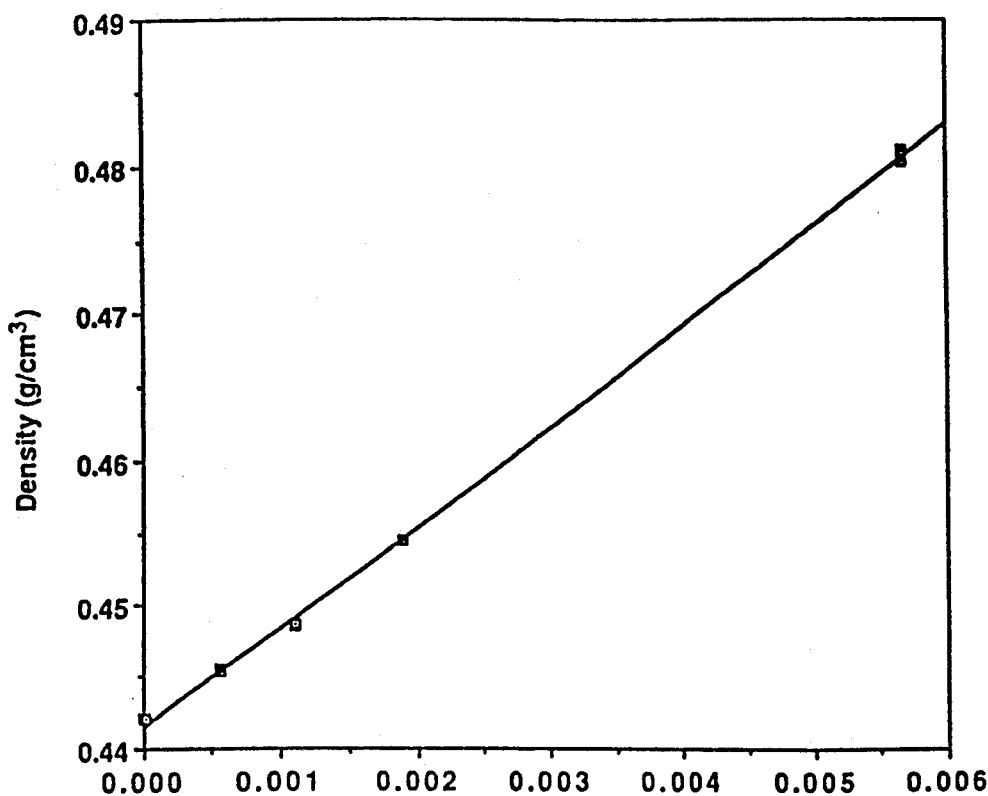
FIG. 8
FIG. 9
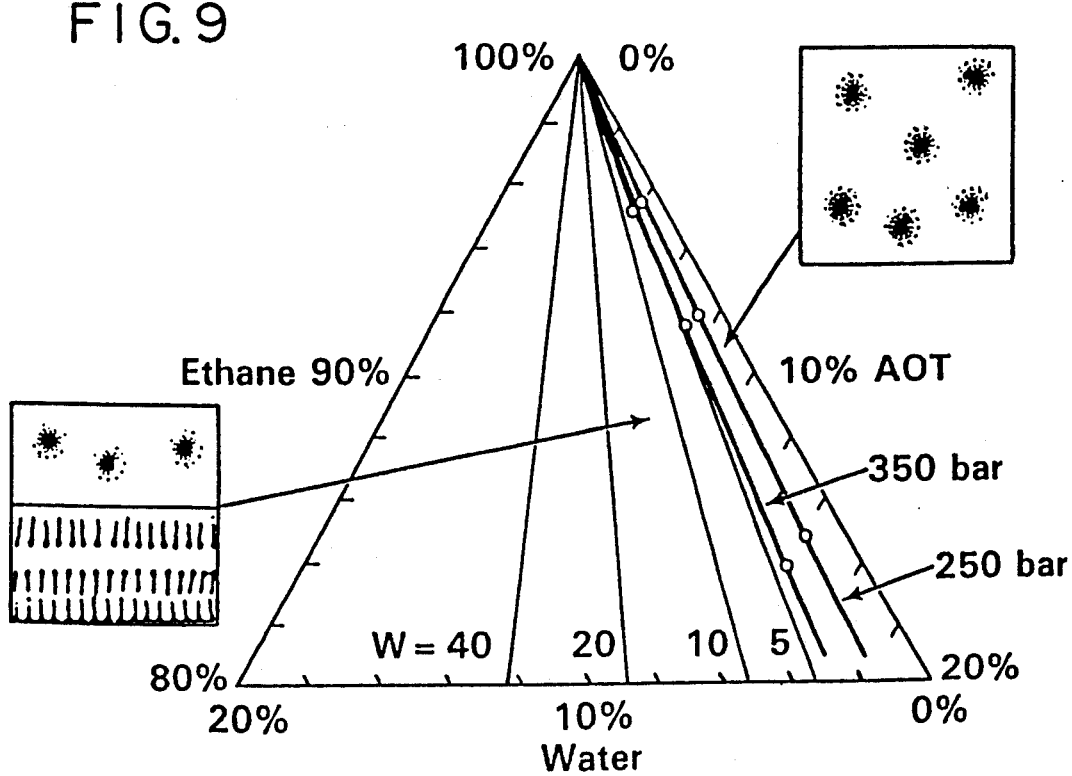

FIG. 14
1. SUPPERCRITICAL ETHANE
   T = 37° C, P = 250 atm
2. AOT
3. WATER
4. POLAR DYE
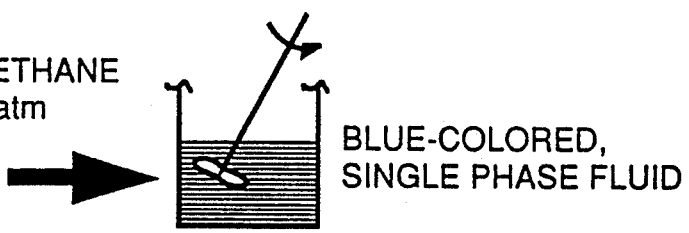
BLUE-COLORED, SINGLE PHASE FLUID
1. SUPPERCRITICAL ETHANE
   T = 37° C, P = 250 atm
2. AOT
3. POLAR DYE
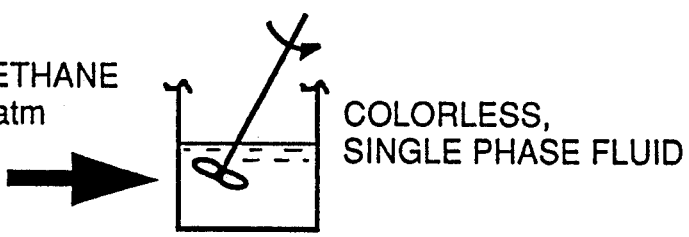
COLORLESS, SINGLE PHASE FLUID
1. SUPPERCRITICAL ETHANE
   T = 37° C, P = 250 atm
2. WATER
3. POLAR DYE
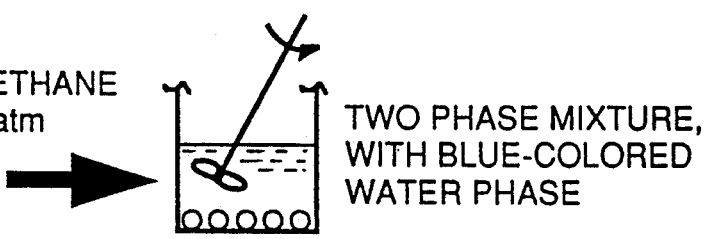
TWO PHASE MIXTURE, WITH BLUE-COLORED WATER PHASE
( ETHANE, TC = 32° C, PC = 48 atm )

2 PARTS REVERSE MICELLE SOLUTION
( AOT ) = 50mM

1 PART AQUEOUS PROTEIN SOLUTION
pH =5-9, ( Na+ ) = 0.011-0.4M

PENTANE REVERSE MICELLE EXTRACTIONS

1. SHAKE FOR ONE HOUR
2. CENTRIFUGE FOR 1/2 HOUR
3. MEASURE UV-VIS SPECTRA OF BOTH PHASES.
4. T = 25° C, P = 1 BAR

PROPANE REVERSE MICELLE EXTRACTIONS

1. STIR FOR 15 MIN.
2. LET SETTLE FOR 10 MIN.
3. MEASURE UV-UIS SPECTRA OF MICELLE PHASE.
4. T = 25° C, P = 10-350 BAR.

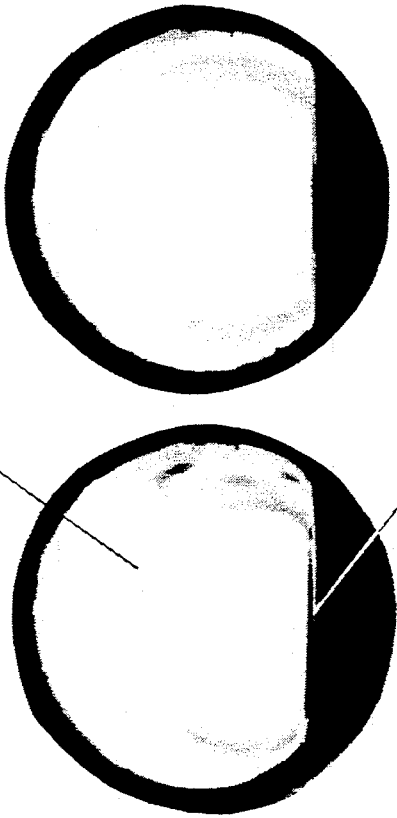
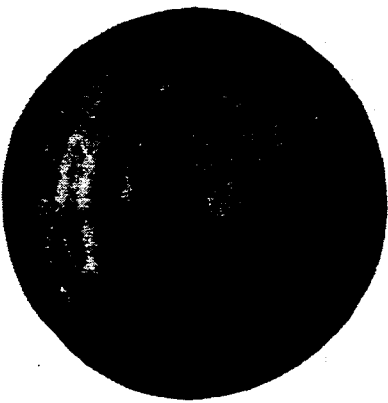
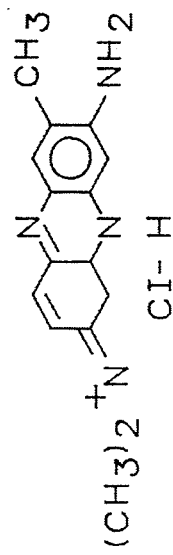
FIG. 18

SUPERCRITICAL FLUID REVERSE MICELLE SEPARATION

The United States has rights in this invention under Department of Energy Contract DE-AC06-76RLO-1830.

This application is a division of application Ser. No. 07/559,396, filed Jul. 25, 1990, now U.S. Pat. No. 5,158,704, which is a continuation of U.S. Ser. No. 07/152,256, filed Feb. 4, 1988, now abandoned.

CROSS REFERENCE TO RELATED APPLICATION

This application is related to commonly-assigned U.S. patent application Ser. No. 125,842, filed Nov. 24, 1987, by D. W. Matson, J. L. Fulton and R. D. Smith, entitled CHEMICAL REACTIONS IN SUPERCRITICAL FLUID MICELLE SYSTEMS.

BACKGROUND OF THE INVENTION

This invention relates generally to the field of colloidal chemistry and more particularly to reverse micelles and microemulsions.

Reverse (or inverted) micelles are small, dynamic aggregates of surfactant molecules surrounding a polar (typically aqueous) core dispersed in a nonpolar continuous (oil) phase. Reverse micelle solutions are clear and thermodynamically stable; as water is added to a reverse micelle solution a microemulsion is formed which contains nanometer-sized water droplets dispersed in a continuous oil phase. There is increasing interest in utilizing reverse micelle and microemulsion solutions for enhanced oil recovery (1,2), for the separation of proteins from aqueous solutions (3, 4, 8), as reaction media for catalytic (5, 23) or enzymatic (6) reactions and as mobile phases in chromatographic separations, and for polymerizations (5, 14).

The surfactant sodium bis(2-ethylhexyl) sulfosuccinate (AOT) forms reverse micelles in nonpolar fluids or oils without addition of a cosurfactant, and thus it is possible to study simple water/AOT/oil three component systems. To determine micelle (and, implicitly, microemulsion) structure and behavior in water/AOT/oil systems, investigators have studied a wide range of properties including conductivity (9), light (10), x-ray and neutron (11) scattering, and solution phase behavior (10). From information of this type one can begin to build both microscopic models and thermodynamic descriptions of these macroscopically homogeneous, but microscopically heterogeneous, micellar solutions.

Studies of reverse micelle solutions to date have been in liquids at temperatures well below the critical temperature ($T_c$) of the continuous phase. For example, the critical temperature of iso-octane, which has been widely studied for AOT reverse micelles, is 288° C. and the critical pressure ($P_c$) is 45 bar. At moderate temperatures the low molecular weight hydrocarbons, such as ethane ($T_c=32°$ C., $P_c=48$ bar) and propane ($T_c=97°$ C., $P_c=42$ bar), can exist as supercritical fluids. For a pure component, the critical point represents the maximum temperature and pressure at which a two-phase single component system (liquid and vapor) can exist in equilibrium. In the supercritical fluid region, where temperature and pressure are above those at the critical point, the properties of the fluid are uniquely different from either the gas or liquid states (12, 13), but roughly variable with fluid pressure (or density) between the two limits. In particular, the solvating power of a supercritical fluid can be continuously varied over a wide range by adjusting fluid pressure. Additionally, the viscosities of supercritical fluids are typically 10 to 100 times higher (13) than gases but much less than those of liquids.

Researchers in this field are not known to have used supercritical or near critical fluids for the continuous phase of reverse micelles or microemulsions. Supercritical fluids have not been considered. Apparently, since supercritical fluids are dense gases, they have been overlooked or considered incapable of forming reverse micelle systems.

SUMMARY OF THE INVENTION

We have discovered that reverse micelle phases can exist in supercritical fluids and that such reverse micelles and microemulsions have unique, useful properties in the supercritical fluid phase and under near critical conditions. These include: (1) the ability to effect a change of phase behavior of the reverse micelle system by variation of the density with changes in pressure or temperature, (2) the ability to effect a change in micelle size or micelle cluster size by variation of the density, (3) the high diffusivities of solutes and micelles in near critical and supercritical fluids, (4) the ability to control selectivity for a specific solute by variation of density.

Solubility, conductivity, light scattering, and density measurements combined with view cell studies confirm the existence of reverse micelle phases in supercritical fluids. The picture of the aggregate structure in fluids is consistent with one of a typical reverse micelle structure, dispersed in a supercritical or near critical continuous phase.

The reverse micelle phase behavior in supercritical fluids is markedly different from the behavior in liquids. Increasing fluid density causes the maximum amount of solubilized water to increase. The phase behavior of these systems may be attributed, in part, to packing constraints of the surfactant molecules and possibily the solubility of large micellar aggregates in the supercritical fluid phase. A relationship between maximum micelle size and fluid density has been postulated on the basis of thermodynamic considerations.

There are a number of important potential applications of a micellar phase in supercritical fluids which utilize the unique properties of the supercritical fluid phase. Many advantages are also obtained for near-critical fluid continuous phasereverse micelle systems. The application of these systems in chromatography and the use of these systems for protein separations or extractions are examples described below. In addition, chemical reactions can be carried out in such systems (see our prior application with D. W. Matson, referenced above). Further, applications are also envisioned, for instance, polar catalysts or enzymes could be molecularly dispersed in a nonpolar gas phase via micelles, opening a new class of gas phase reactions. Since diffusivities of reactants or products are much greater in the supercritical fluid continuous phases compared with liquids, high transport rates to and from active sites in the catalyst-containing micelle may increase reaction rates for those reactions which are diffusion limited. The recovery of product or catalyst from the micelle core may be simplified since the micelle size, and even the existence of a reverse micelle phase, is dependent on fluid pressure. This is in contrast to liquid systems where pressure has little effect on phase behavior at up to 1000 bar.

The discovery of reverse micelle structures in supercritical fluids creates an opportunity to investigate the properties of micelle solutions using a new thermodynamic tool: the variable density and solvating power of the low molecular weight supercritical continuous phase. The study of aggregate formation in solution is important in the separate fields of supercritical fluid solvation and microemulsion properties, and a common goal is that of describing intermolecular forces responsible for forming these structures. The clustering of solvent molecules around a solute molecule is an important mechanism of solubilization in supercritical fluids, as has been shown in recent spectroscopic studies (15). A description of the type and magnitude of forces which create molecular aggregates is presently an area of intense research activity.

The supercritical or near-critical nonpolar or low-polarity fluids of interest are gases under standard temperature-pressure conditions. In accordance with the invention, these fluids are maintained in a temperature and pressure range such that the continuous-phase fluid has a density at least as great as its critical density. These fluids include alkanes up to butane, $CO_2$, $N_2O$, $SF_6$, Xe, alkenes such as ethylene and propylene, acetylene and a number of chorinated and fluorinated hydrocarbons such as $CF_3CL$ and $CF_3H$. Mixtures of these gases, and the addition of other fluid modifiers or cosurfactants, are also included. The polar fluid in most cases of interest is water or an aqueous solution, but can be or include another polar fluid such as DMSO.

The invention has a wide range of applications, generally including a variety of chemical reactions and extraction and separation processes. It has a number of advantages over conventional liquid reverse micelle and microemulsion systems, generally including:

1. Faster separation, extraction and reaction rates because of the enhanced mass transport properties of supercritical and near-critical fluids. Diffusivities of solutes and micelles can be 5-100 times higher in near critical liquids and supercritical fluids than they are in liquids.

2. The ability to manipulate reaction pathways (i.e., selectivity) or rates by varying system pressure.

3. The ability to recover products or catalyst after separation or reaction by changing system density by adjusting temperature or pressure.

4. The ability to separate mixtures, and control selectivity of separation, by varying system density.

5. The ability to extract solutes from liquid or solid phases at high rates, with the added advantage that these low molecular weight near-critical liquids and supercritical fluid have very low solubility in the media to be extracted and the large density difference between these systems and the liquid or solid phases which have been extracted greatly augments the recovery of each of these two phases after separation.

In a specific application of the invention, reverse micelle chromatography decreases retention times for polar solutes with silica stationary phases. Other stationary phases may also be used. The most valuable chromatographic applications are envisioned to be process chromatography (i.e., larger scale than analytical applications). In applications to separation or extraction of biological and biochemical compounds, the invention offers a wide range of options for separation processes, utilizing selective uptake of the biological/biochemical components into the reverse micelle phase and phase separation by manipulation of the maximum polar fluid-to-surfactant ratio ($W_o$) by control of density. Some near critical nonpolar fluids that are gases at standard temperature and pressure, such as propane, can be used under pressures in which they are liquids, and so controlled, at temperatures safe for thermally-sensitive biological compounds. Other fluids under supercritical conditions may also be advantageous. This method is shown to be effective for selectively extracting proteins, such as hemoglobin, myoglobin, and cytochrome-C, using density control contrary to experience in liquid AOT/iso-octane reverse micelle separations (3). Such separations can be conducted without substantial loss of activity or denaturing of proteins.

The foregoing and additional objects, features, and advantages of the present invention will be more readily apparent from the following detailed description of a preferred embodiment which proceeds with reference to the accompanying drawings.

BRIEF DESCRIPTION OF THE DRAWINGS

FIG. 1 is a diagram of an idealized reverse micelle structure.

FIG. 2 shows six ternary phase diagrams for alkane-AOT-water systems: (a) liquid ethane; 25° C., (b) supercritical ethane, 37° C. (c) liquid propane, 25° C., (d) supercritical propane, 103° C., (e) liquid iso-octane, 25° C., and (f) liquid iso-octane, 103° C. In the region to the right of the phase boundary lines a single, clear reverse micelle phase exists; in the region to the left the system contains two phases.

FIG. 8 is a graph of density of AOT-supercritical ethane solutions at 37° C. and 240 bar.

FIG. 9 is an enlargement of FIG. 2(b) showing the ethane-rich corner of the ethane/AOT/water ternary phase diagram (weight %) at 37° C. and at two pressures, 250 and 350 bar.

iso-octane, (B) malachite green, (C) oxazine perchlorate.

FIG. 14 is a series of diagrams comparing single- and two-phase reverse micelle systems containing a polar dye and supercritical ethane.

Figure 15:
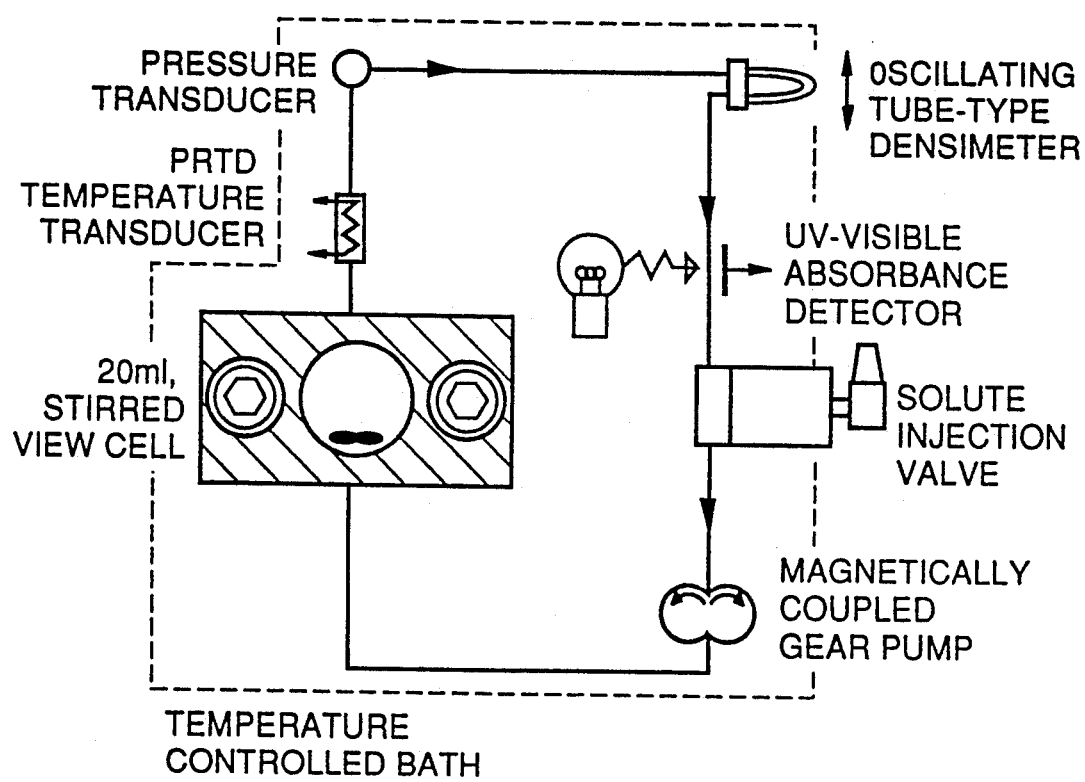

FIG. 15 is a diagram of a supercritical fluid view cell and in-line analytical instruments.

Figure 16:
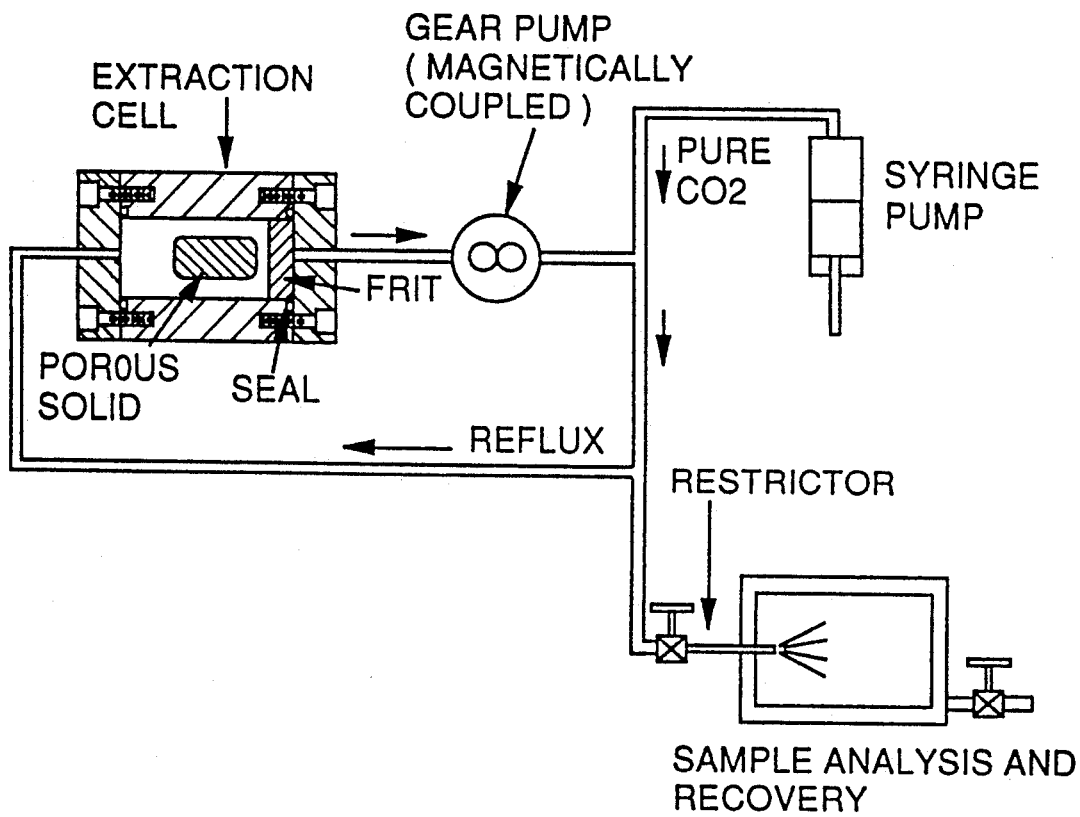

FIG. 16 is a block diagram of supercritical fluid extraction evaluation equipment.

Figure 17:
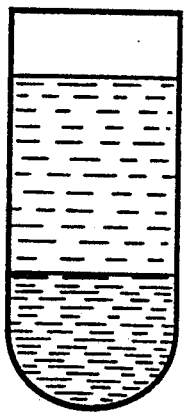

FIG. 17 is a diagram of a near supercritical reverse micelle system in accordance with the invention.

Figure 19:
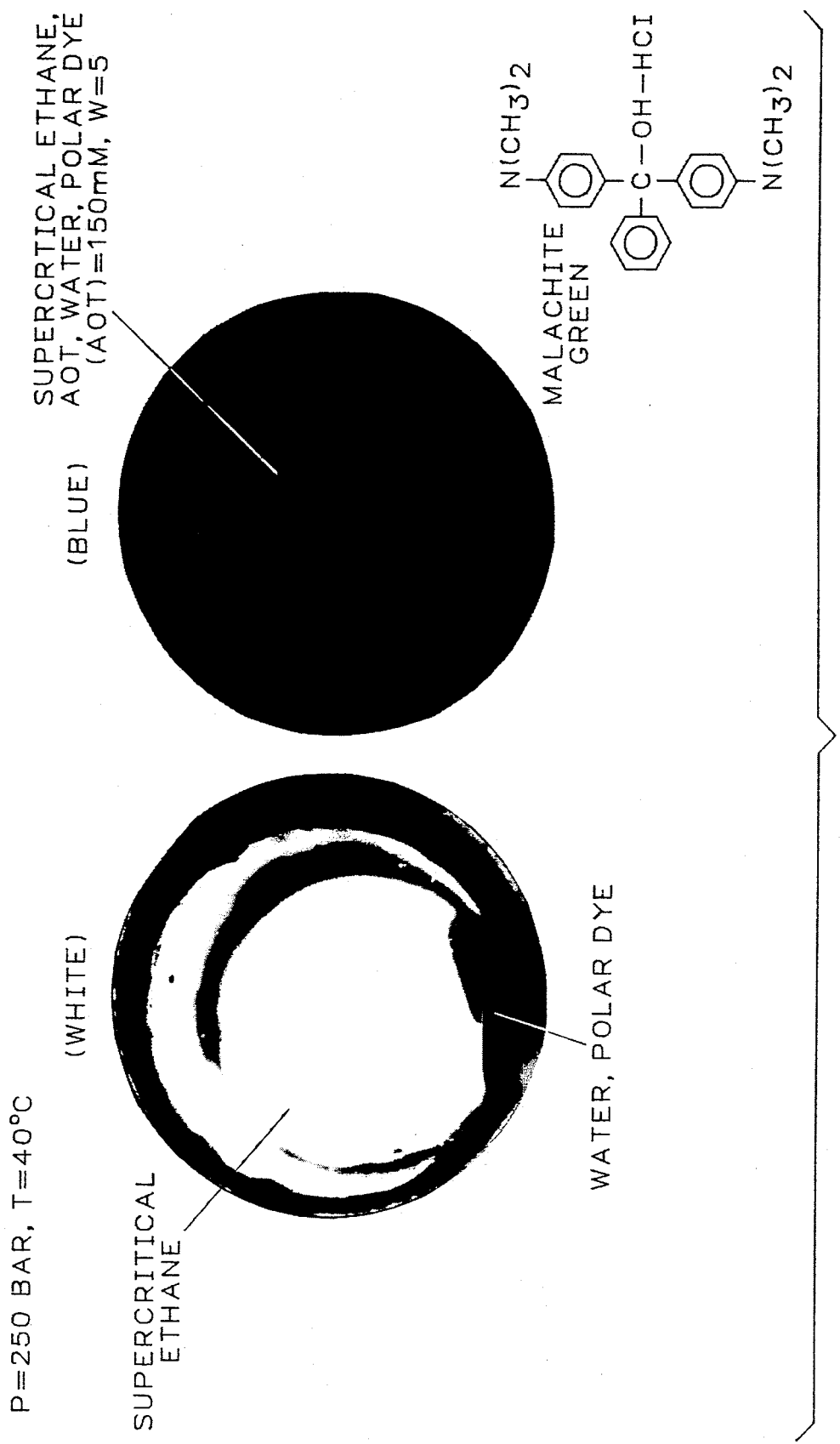

FIGS. 18 and 19 are diagrams showing solubilization of water and a polar dye by reverse micelle propane and ethane systems in accordance with the invention.

Figure 20:
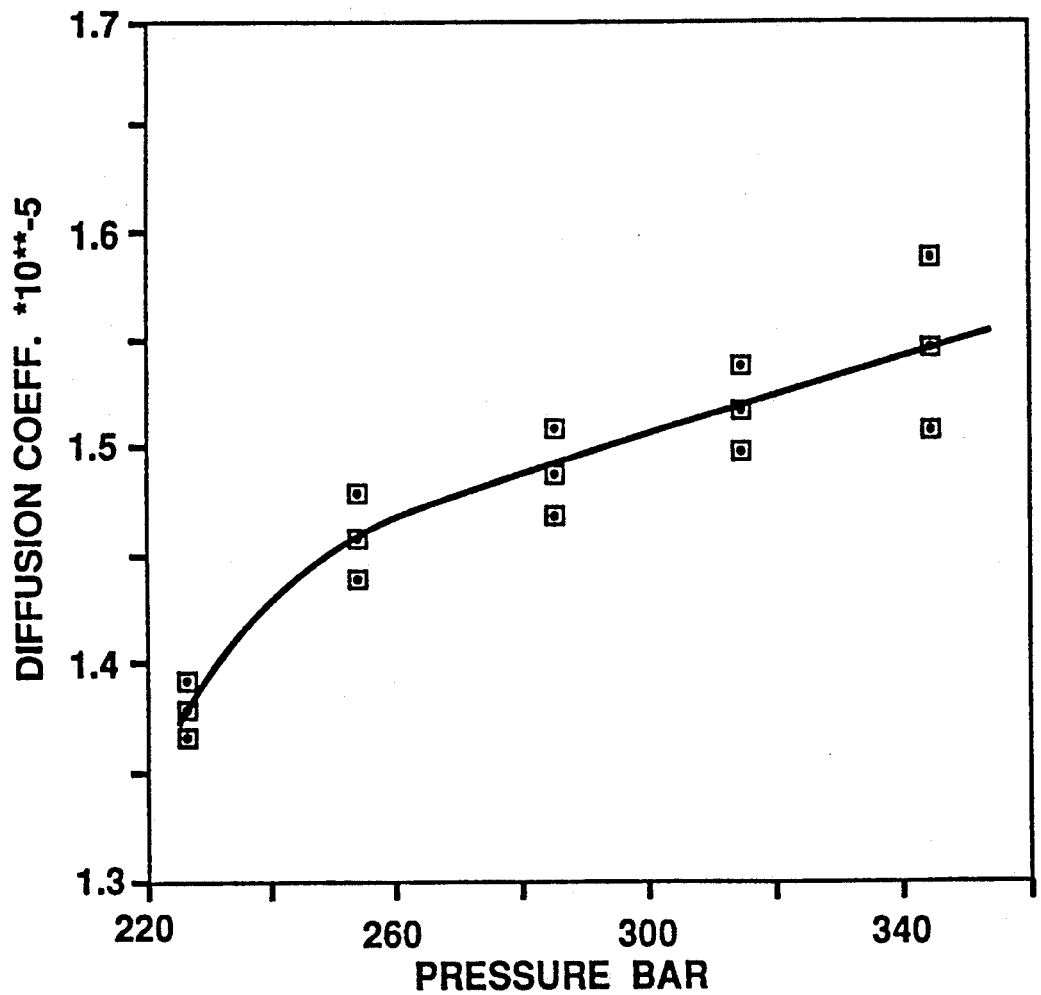

FIG. 20 is a graph of diffusion coefficient vs. pressure for AOT/ethane at 37° C.

Figure 21:
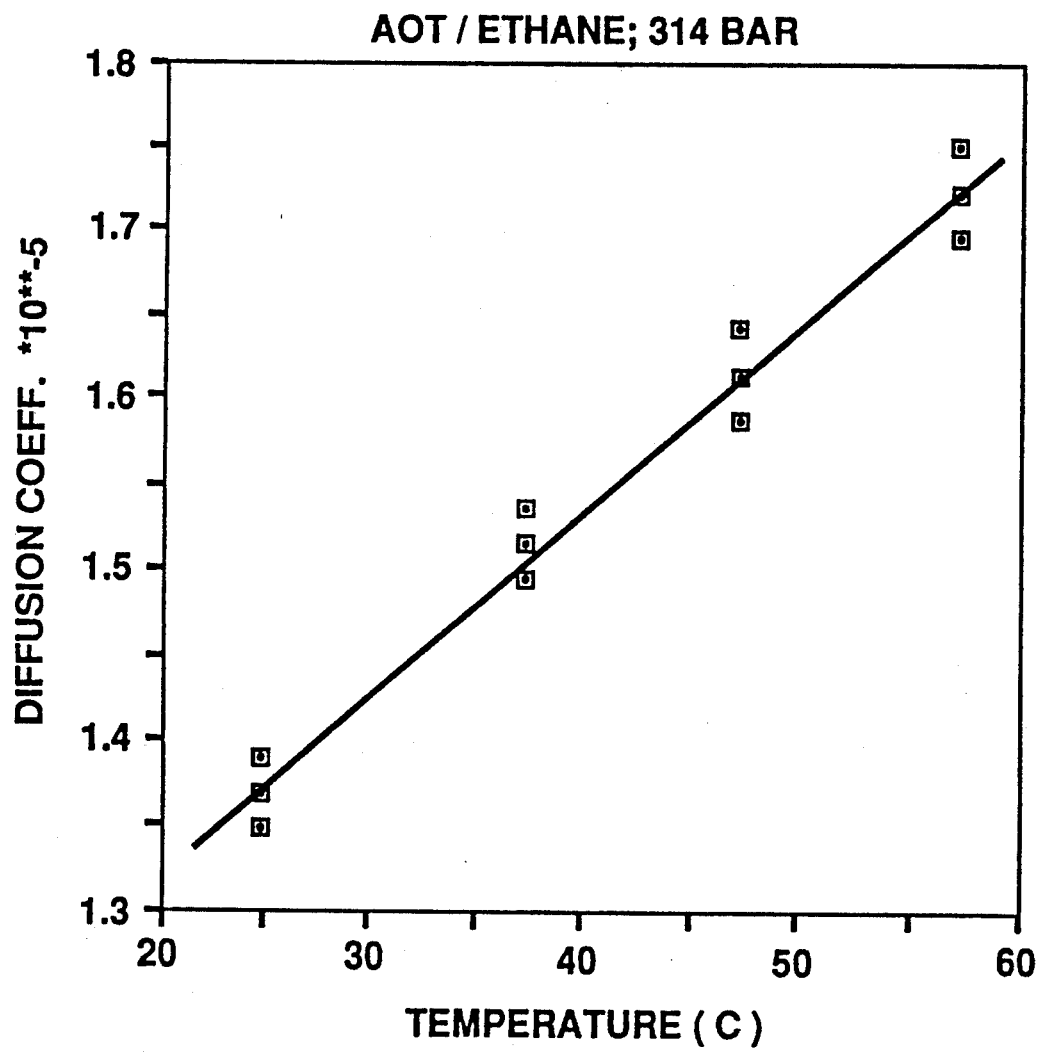

FIG. 21 is a graph of diffusion coefficient vs. temperature for AOT/ethane at 314 bar.

Figure 22:
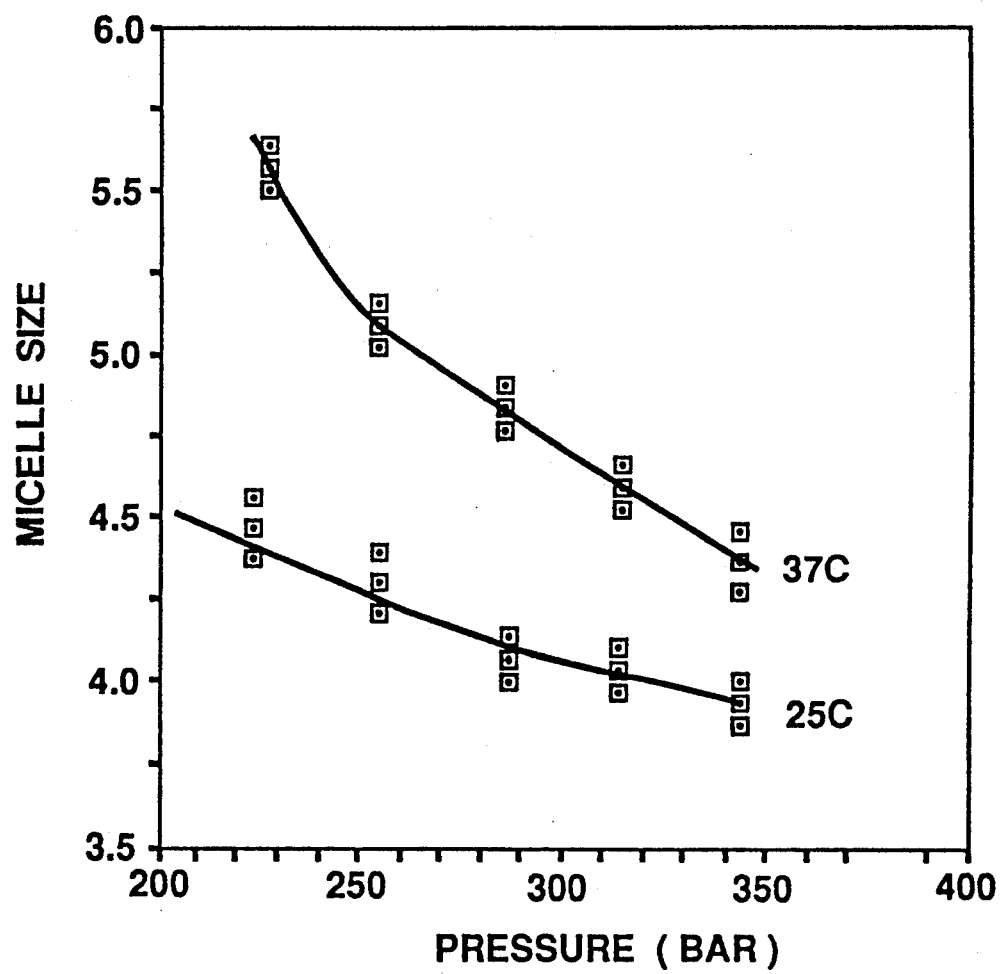

FIG. 22 is a graph of micelle size vs. pressure for AOT/ethane at 25° C. and at 37° C.

DETAILED DESCRIPTION

General Description

In accordance with the invention, reverse micelles can be formed in which a supercritical or near critical nonpolar or low-polarity fluid that is a gas at STP constitutes the continuous phase. Micelles are thermodynamically stable dynamic aggregates, which are optically transparent and typically under 80 angstroms in diameter. Microemulsions can be somewhat larger. A typical reverse micelle structure is shown in FIG. 1. The aqueous or polar phase inside the micelle can solvate a range of organic and inorganic species including proteins, enzymes or catalyst molecules which are generally insoluble in the nonpolar or low-polarity continuous phase.

The nature of supercritical fluids and near-critical liquids such as propane allows the solution properties (including density, diffusion coefficient, viscosity, solvating power, dielectric, conductivity, etc.) of the continuous phase to be easily manipulated by simply changing density (temperature and pressure). This control over solvent properties also provides an important adjustable parameter for the manipulation of reactions involving reverse micelle systems. It has been shown that the maximum water to surfactant ratio ($W_o$) depends strongly on pressure (density); since $W_o$ is related to both the maximum size and solvent properties of the reverse micelle, potential changes in reactivity or solvating power are reasonable. The anticipated benefits of supercritical and near-critical fluid-reverse micelle reaction media are: (1) a combined polar and nonpolar reaction environment which will be favorable for producing a wide range of products, (2) the reaction rates may be more than 100 times faster than in liquids, (3) a convenient means for recovering the enzyme (or catalyst) and reaction products, and (4) development of continuous processing methods is much simpler due to the ability to induce a phase separation at any time.

Reverse micelles and microemulsions have been created in our initial studies using (among others) an anionic surfactant (Aerosol-TO or AOT) with near-critical and supercritical fluids such as ethane or propane (T=25 −110° C., P=10-350 bar).

However, a wide range of fluids and surfactants may be used to produce such systems (including catonic, zwitterionic and nonionic surfactants), each having potential advantages in certain applications. The water to surfactant ratio largely determines the size of the micelle. In most systems, a maximum water to surfactant ratio ($W_o$) exists, which can be ascribed to geometric constraints imposed by surfactant orientation and solvation by the continuous (supercritical fluid) phase. Reverse micelles have a polar core, with solvent properties dependent upon the [water]/[surfactant] ratio (W), which can solvate highly polar water soluble compounds (e.g. hydrophilic substances such as proteins, enzymes, chemical catalysts and initiators) and even normally insoluble amphiphilic compounds. At low W values (<8 to 10) the water in the micelle is highly structured due to association with the AOT sulfonate groups and the counter ion core, and the environment in the micelle core resembles that of an ionic fluid due to the large counter ion concentration. At larger W values (>10 to 15) the swollen micelles (or microemulsions) have a free water core which provides a distinct third solvent environment and which approaches the properties of bulk water at large W. Certain enzymes and polar compounds are only solubilized by reverse micelles swollen by significant quantities of water, (W>10).

Reverse micelles (and, implicitly, microemulsions) can be visualized as submicroscopic containers or reaction vessels providing enormous interfacial areas and solvent environments appropriate for large or complex reactant species. The surfactant concentration and W value determines the number and density of reverse micelles. The micelles are dynamic structures which collide, coalesce, and exchange contents efficiently on a time scale of $10^{-10}$ to $10^{-6}$ seconds. The details of reverse micelle interactions with surfaces are currently unknown, but we have demonstrated that reverse micelle contents can be exchanged efficiently with surfaces from both liquid and supercritical systems. Reverse micelles are typically spherical, although other structures (e.g., rods) can be favored under certain conditions (typically high surfactant concentrations). Reactants or catalytic species will often be oriented relative to the micelle surface (particularly at low W), providing the basis for much greater selectivity in reaction processes or protection of normally reactive functional groups.

It has been demonstrated that many catalysts or initiators can be dissolved in liquid reverse micelle systems. In our initial studies we have demonstrated that complex polar compounds such as proteins and enzymes are readily dissolved in nonpolar supercritical solvents in which reverse micelles have been created. Reactions between a catalyst or enzyme contained in the micelle core with a reactant in the supercritical or near critical fluid phase will typically proceed at higher rates than in conventional liquid micelle systems. Similarly, a reactant can exist in the micelle phase or in the continuous fluid phase. Products of reactions can partition to either the continuous fluid phase or the micelle phase allowing separation after a change in pressure. The properties of these systems also offer the possibility of improved reaction selectivity, limiting unwanted by-products.

Ethane, propane, or carbon dioxide ($T_c$=32°, 103°, and 31° C., respectively) are examples of excellent nonpolar fluids for dispersing a micelle encapsulated catalyst, since they can provide both a favorable solvent environment, low critical temperatures, and a means of easily recovering the enzyme and products after the conversion reaction (by manipulation of density). These fluids (on the basis of liquid reverse micelle systems)

should not deactivate (denature) most enzymes, or be converted in the reactions, and yet they act as good organophilic solvents. Hydrogen solubility in ethane, propane, or carbon dioxide is much higher than in alkane liquids (hexane, iso-octane), providing a much more favorable reducing environment for the enzymatic liquefaction. Viscosities of supercritical alkanes and near-critical alkane liquids, for example ethane or propane, are 10–100 times lower than in liquids, and diffusion coefficients are correspondingly higher. The micelle diffusion rates into the pores of a complex substance, such as coal, and product diffusion rates out, are anticipated to be greatly enhanced. The reaction rates would then be correspondingly increased for diffusion limited reactions.

The phase behavior of micelles in supercritical and near-critical fluids provides the basis for unique capabilities for enzymatic reactions, including potentially the liquefaction of coal.

Ternary phase diagrams determined for subcritical (or near-critical liquid) ethane, propane and iso-octane and for supercritical ethane and propane are shown in FIG. 2. Only the alkane-rich corner of the phase diagram is represented, up to a maximum of 20% water or AOT by weight. On each of these diagrams, the location of the phase boundary, in terms of the maximum water to surfactant ratio ($W_o$), is shown for three different pressures. The areas to the right of these $W_o$ lines (phase boundaries) are regions where a clear microemulsion phase exists. To the left of the $W_o$ lines, two phase systems or more complex multiphase systems exist containing either liquid-fluid or liquid-liquid phases. The liquid phases may incorporate complex structures such as liquid crystals.

Reverse micelle phase behavior has been found to be remarkably different in supercritical fluids and near-critical liquids (e.g., ethane and propane) compared to that of liquids far below the critical temperature (e.g., iso-octane). Of particular interest is near-critical liquid propane which shows very large changes in the maximum allowable water content, $W_o$, as the pressure is changed. This phenomena provides several approaches for separations including the ability to precipitate and recover the enzyme or catalyst for a reaction by reducing the maximum micelle size ($W_o$) with an appropriate pressure reduction. In a later step, the reaction products, which have much higher molecular weight than the fluid, can be recovered through further pressure or temperature changes. Methods of control of phase properties used in conventional liquid systems, such as variation of ionic strength or pH, are also adaptable to these systems. A unique feature of the supercritical and near-critical systems is that separations can be conducted by causing the micelle phase to be destroyed in the fluid, forming two phases: a non-aqueous phase containing, for example, a product, and an aqueous phase containing waste and/or water soluble products.

As shown in FIG. 2, supercritical propane, sub- and supercritical ethane also have a pronounced $W_o$ dependence on pressure, although remarkably, to a lesser extent than liquid propane. These fluids cover a wide range of $W_o$ values, from about 3 up to 25. By comparison, liquids such as iso-octane show very little variation in $W_o$ with pressure at both 25° and 103° C.

Our research has shown that reverse supercritical micelles can be created or destroyed by adjusting density through pressure and temperature changes. Since reverse micelle existence appears related to the solubility of the surfactant in the supercritical fluid and thus the fluid density, it is possible that a distinct critical micelle fluid density may exist. These studies have also indicated that the maximum water to AOT ratio ($W_o$), of the near-critical and supercritical micelles is also highly pressure dependent, providing the basis for easy manipulation of the reaction environment. Supercritical reverse micelles should also simplify product or catalyst recovery after reaction by providing the control necessary to "empty" the micelles or for product fractionation from the supercritical fluid phase.

Specific advantages associated with enzymatic or catalytic processes, and many reaction processes in general, in supercritical and near-critical fluid-micelle phases include:

(1) The polar environment of the reverse micelle (20–100 angstrom diameter) hosts enzymes or catalysts.

(2) the activity of the enzyme or catalyst in the micelle core may be altered by changing the reaction environment by manipulating the size or shape of the micelles with changes in fluid density.

(3) Improved reaction rates due to the rapid diffusion and pore penetration of micelles to reaction sites, inside porous substrates (e.g., coal particles) and the rapid product diffusion away from the reaction site. Solute diffusion rates are typically 10–100 times higher in supercritical fluids than in liquids.

(4) Reactants, enzymes or catalysts in the micelle interfacial region may be oriented with respect to the micelle surface, providing the basis for improved selectivity (i.e., more a desirable product).

(5) Improved product or catalyst recovery is expected based on the demonstrated ability to "empty" the micelle core with a small change in pressure. For products partitioned into the fluid phase, recovery is easily accomplished by adjusting the solvating power of the fluid with pressure or temperature.

(6) Near- and supercritical fluids are excellent solvents for hydrogen and other gases, providing a reducing environment for a liquefaction reaction.

Since reverse micelle supercritical fluid solvents constitute novel reaction systems, it is likely that new insights will be developed which will provide other unique possibilities not anticipated at the present time.

Initial Studies and Conclusions

Our initial studies have explored reverse micelles using surfactant sodium bis(2-ethylhexyl) sulfosuccinate or Aerosol-TO (AOT) with various supercritical fluids and near critical fluids as the continuous phase. However, a range of other surfactants and including co-surfactants, are also amenable to forming reverse micelles depending upon the nature of the nonpolar or low-polarity continuous phase. Supercritical fluids provide variable properties which extend from the gas to near-liquid phase limits and which can be readily manipulated by pressure or temperature since the density of the fluid is strongly affected by both these parameters. The variable solvent properties include viscosities and diffusion rates (also dependent upon fluid density) which are intermediate between the gas- and liquid-phase values, (12, 13) Supercritical reverse-micellar solutions combine the high diffusivities and variable (organophilic) solvating power of the supercritical fluid with the (hydrophilic) solvating ability of the reverse micelle. The transport properties of such systems are expected to be primarily governed by the fluid pressure with the micelles or microemulsions contributing what amounts to a second, suspended, highly polar phase to the solvent. Thus, we anticipate that supercritical fluids would provide novel control of the solvent properties of the continuous nonpolar phase of reverse-micelle systems, providing the basis for new applications. Micelles also extend applicability of processes based upon supercritical fluids to highly polar and labile compounds which would be otherwise impractical due to low solubility. (12, 14, 15)

One primary experimental method utilized to determine the presence of reverse micelles was visual observation of the solvation of highly polar, colored azo dyes (malachite green [p,p'-(p-phenylmethylidene)bis(N,N-dimethylaniline] and methyl red [2-[p-(dimethylamino)-phenyl]azo]benzoic acid] or a protein (cytochrome C) in supercritical fluid-AOT-water systems. Solubilization of malachite green and cytochrome C into liquid alkane reverse micelles has been previously reported. (3, 8, 24) These substances were determined to have negligible solubility in both the supercritical hydrocarbon and the supercritical hydrocarbon saturated with water in the absence of the surfactant. A number of additional supercritical fluids have been briefly examined ($CF_3Cl$, $SF_6$, $CO_2$, $N_2O$); however, AOT reverse micelles were formed at only moderate pressures in hydrocarbon solvents (e.g., ethane, propane, n-butane, and n-pentane), which our initial studies have examined in greatest detail. The choice of surfactant depends largely on the composition of the continuous phase. Both surfactant mixtures and fluid mixtures (e.g., $C_2H_6$ and $CO_2$) can be used. In addition to visual studies, solution densities as a function of temperature and pressure, were measured using a Mettler Model DMA 511 densimeter. The formation of reverse micelles was investigated as a function of temperature, pressure, and surfactant concentration, to partially define the relevant phase diagram boundaries. Extension of visual studies to supercritical pentane exceeded the thermal stability limit of AOT (about 150° C.) due to hydrolysis. Reverse micelles in liquid pentane were observed to this temperature at elevated pressures. To confirm the presence of micelles in supercritical pentane, a fluorescence capillary flow cell arrangement (as typically configured for chromatographic detection) was used which minimized the time at elevated temperatures.

In all the supercritical alkane systems studied, the dissolution of AOT (at low water concentrations) occurs in three stages as the fluid density increases. At low fluid densities, three phases exist; solid AOT, a viscous AOT-alkane liquid mixture, and a gaseous alkane upper phase. At intermediate densities, an AOT-alkane liquid phase exists in equilibrium with a predominantly gaseous alkane upper phase. Finally, at higher densities a single micelle-containing phase is formed. As water is added to this phase, the micelles are "swollen" to sizes which accept the polar dyes. As the density of this solution is slowly reduced, a sharp phase transition occurs with precipitation of a second dye-containing phase and the apparent destruction of the micelle phase.

The propane-AOT-water system at higher pressures was in many respects similar to larger liquid alkane systems. Solubility of the AOT monomer in liquid propane (at 125° C. and pressures slightly above its vapor pressure) is similar to that in typical hydrocarbon solvents (about $4 \times 10^{-4}$ M). A key property of reverse micelles is the water-to-AOT ratio, $W_o[H_2O]/[AOT]$, since for $W_o < 10$ the water molecules have solvent properties influenced by interaction with the surfactant while a larger $W_o$ results in a water core which approaches conventional solvent properties. (6, 24-26) Table 1 gives the maximum $W_o$ values for supercritical alkane-AOT-water systems.

TABLE 1

Comparison of the Maximum $W_o$ for Various n-Alkanes

| | $T_c{}^d$°C. | $P_c{}^d$bar | $W_o$(max) |
|---|---|---|---|
| supercritical ethane[a] | 32.4 | 48.0 | 5 |
| supercritical propane[a] | 97.0 | 43.3 | about 10 |
| liquid propane[b] | 97.0 | 43.3 | about 20 |
| liquid pentane[b] | 196 | 33.2 | 22 |
| liquid octane[c] | 296 | 24.5 | 20 |
| liquid decane[c] | 344 | 20.8 | 30 |

[a]Supercritical fluids investigated in this study (ethane 37° C., 250 bar; propane 110° C., 250 bar).
[b]Liquids investigated in this study (propane 37° C., 250 bar; pentane 25° C., 1 bar).
[c]From ref 11 and 12 (T = 25° C., P = 1 bar).
[d]Critical parameter for n-alkane phase.

$W_o$ values in liquid propane are slightly lower than those reported for n-octane. (27-29) over the temperature and pressure ranges where reverse micelles are found, $W_o$ values in supercritical propane appear to vary significantly from those of the liquid. The minimum pressure observed for micelle formation in propane was about 120 bar at 105° C. Reverse micelles formed in both liquid and supercritical propane were observed to solubilize large, hydrophilic molecules such as cytochrome C (MW=13000).

Micelle formation in supercritical ethane was markedly different than in the larger alkanes and was studied in greater detail. Addition of supercritical ethane to a surfactant-water mixture at lower pressures results initially in uptake of some ethane into the condensed phase. As density is further increased, by addition of ethane, a single phase containing micelles results. At a fixed temperature (37° C.) and pressure (250 bar) the reverse-micelle formation depends on the AOT and water concentration as shown in FIG. 9. $W_o$ in supercritical ethane at these conditions exhibits behavior different from larger liquid n-alkane systems.(30) First, the maximum $W_o$ is more dependent on AOT concentration; second, $W_o$ is much lower than for other hydrocarbon systems. The low $W_o$ values observed in both supercritical ethane and propane are tentatively explained in terms of the "packing ratio" model described by Mitchell and Ninham. (20, 22) The area occupied by the polar head groups remains constant at fixed pH and ionic content. In contrast, the greater penetration of the surfactant tails and the larger volume solvated by the supercritical fluid result in an interfacial surfactant layer which will have higher curvature; thus only smaller micelles can exist.

Figure 4:
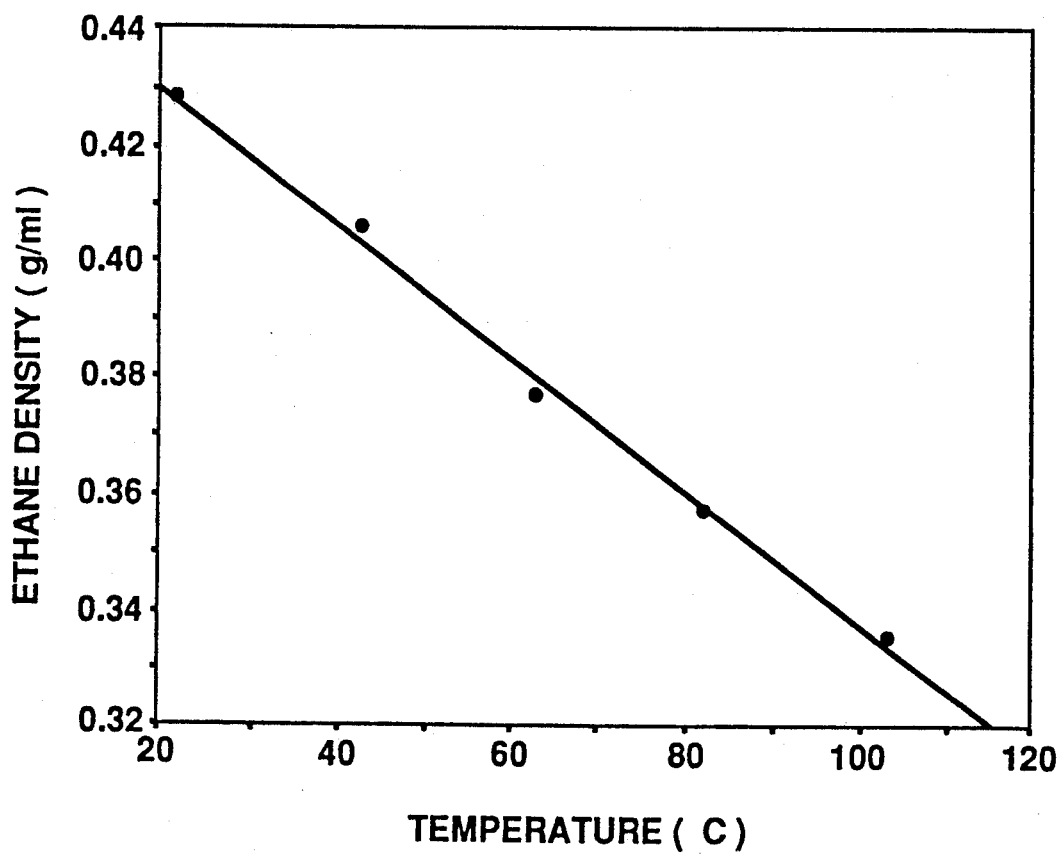
FIG. 4 is a graph of a minimum supercritical ethane ($T_c = 32.4°$ C.) density required for the formation of stable reverse micelles as a function of temperature. Densities correspond closely to those for the pure ethane at similar conditions.

As the supercritical ethane density is reduced, the single micellar phase is destroyed and two phases are formed consisting of an AOT-water-rich liquid phase and a predominantly ethane upper phase. As shown in FIG. 4, the minimum ethane density for micelle stability decreases as the temperature is increased; this suggests that the increase in thermal energy is sufficient to offset the loss of ethane solvating power at the lower fluid density. The density range over which dissolution and micellization occurs differs for subcritical liquid and supercritical ethane; this can also be attributed to the temperature difference of the two phases.

There are several interesting technological applications of supercritical fluid or near critical liquid micelles or microemulsions. Diffusion coefficients are up to $10^2$ higher in the continuous supercritical fluid phase than in liquids. Similarly, viscosity is up to $10^2$ lower in such fluids. This combination of properties should allow very high mass transfer rates in extractions from liquid or porous solid phases or high overall rates for interfacial reaction processes. By changing the size or shape of the reverse micelle by varying the fluid density, the selectivity of the micelle core in extractions or the properties of the micelle environment for chemical reactions can be changed. Also, supercritical fluid density is a much less constrained variable than temperature in controlling micellar phase behavior; in contrast to liquid systems where pressure and temperature have only moderate utility. A small decrease in density could be used to alter the phase behavior and thus "unload" the micelle contents for final product recovery after extraction. The step could be reversed by a small increase in density to rapidly reform the micelles. Equivalent control is absent in liquid systems where ionic strength or pH are typically used to manipulate phase behavior. Further studies are in progress aimed at both the investigation of reverse-micelle phase behavior and properties and the development of separation and chromatographic processes utilizing the unique solvating characteristics of both the supercritical fluids and reverse-micellar phases.

Density-Dependent Properties of AOT/Water/Supercritical Ethane and Propane

In the following section, we examine in more detail the properties of surfactant aggregates in supercritical ethane and propane, focusing on the single-phase microemulsion region containing 80 to 100% by weight ethane or propane. We present the results of solubility measurements for AOT in pure ethane and propane and results of conductivity and density measurements of supercritical fluid reverse micelle solutions. The effect of temperature and pressure on phase behavior of AOT/water/supercritical ethane or propane ternary mixtures are also examined. The phase behavior of these systems is strongly dependent on fluid pressure, in contrast to liquid systems where similar changes in pressure have little or no effect. The new evidence supports and extends our initial findings related to reverse micelle structures in supercritical fluids, and we report properties of these systems which suggest the potential for important practical applications.

EXPERIMENTAL SECTION

Materials

The surfactant AOT was obtained from Fluka (>98%, "purum") and was further purified according to the method of Kotlarchyk (16). In the final step, the purified AOT was dried in vacuo for eight hours. The molar water-to-AOT ratio, $W=[H_2O]/[AOT]$, was taken to be 1 in the purified, dried solid (16). Solutions of 50 mM AOT in iso-octane had an absorbance of less than 0.02 A.U. at 280 nm which compares favorably with AOT purified by HPLC[6]. Potentiometric titration indicated that acid impurities were less than 0.2 mole percent (6). The purified AOT was analyzed by mass spectrometry using 70 eV electron ionization of the sample using direct probe introduction. Two trace impurities were identified: 2-ethyl-1-hexanol and maleic acid. The ethane and propane were both "CP" grade from Linde. The iso-octane (GC-MS grade) was used as received from Burdick and Jackson. Distilled, deionized water was used throughout.

Equipment

The phase behavior of the AOT/water/supercritical fluid systems was studied using a high pressure stainless steel view cell having a ⅜ in. diameter by 3 in. cylindrical volume, capped on both ends with 1 in. diameter by ½ in. thick sapphire windows. Silver plated metal "C" ring seals (Helicoflex) formed the sapphire to metal seal. The fluid mixtures were agitated with a ½ in. long Teflon-coated stir bar driven by a magnetic stirrer (VWR, Model 200). The insulated cell was heated electrically. Temperature was controlled to +/−0.1° C. using a three-mode controller with a platinum resistance probe (Omega, No. 2180A, +/−0.3° C. accuracy). The fluid pressure was measured with a bourdon-tube pressure gauge (Heise, +/−0.3 bar accuracy). While stirring, the fluid was allowed to equilibrate thermally for 10 min. before each new reading. In selected studies much longer observation periods (about one day) were used to access the phase stability Of these systems, although equilibria were established rapidly in the systems reported.

Procedure

The procedure for finding a point on the two-phase boundary of the n-alkane/AOT/water systems was as follows. A weighed amount of solid AOT was placed In the view cell and, after flushing air from the cell with low pressure alkane, the cell was filled to within 10 bar of the desired pressure with a high pressure syringe pump (Varian 8500). This AOT/alkane solution was modified by injecting successive 27 ul increments of water until the two-phase boundary was reached. A hand operated syringe pump (High Pressure Equipment, No. 87-6-5) was used to slowly inject the water through a metering valve into the supercritical fluid-reverse micelle solution. By keeping the water in the syringe pump at a constant pressure slightly above the view cell pressure, the amount of injected water could be determined from the vernier scale on the screw of the pump. The same procedure was used to study phase behavior in the liquid iso-octane system., At each temperature, four different AOT concentrations (0.020, 0.050, 0.075, and 0.150 M) were prepared to study phase behavior in the range of pressures from 100 to 350 bar.

The accuracy of the location of the phase boundary determined by the above method was verified using a slightly different technique. The weighed AOT sample was placed in the view cell, along with a predetermined amount of water and pressurized to within 20 bar of the pressure expected to result in a single phase and then stirred for 10 min. The fluid pressure was then increased by 10 bar by adding the alkane and then stirred again for 10 min. This procedure was repeated until a stable single phase system was obtained. The phase boundaries determined for five systems were found to agree within +/−5% of the values determined from the previous measurement technique.

The solution conductivity was measured using a Yellow Springs Instrument conductivity meter (YSI Model 34) with a high pressure conductivity cell. The high pressure cell consisted of ten stacked, 10 mm diameter stainless steel disc electrodes insulated with Teflon washers and had a cell constant of 0.0044 $cm^{-1}$. The conductivity meter is particularly well suited for use with this type of cell since capacitance errors are minimized by the active circuit and since electrode over-potential is eliminated by measurement potentials of less than 1 volt.

The solubility of "dry" AOT ($W<1$) in supercritical ethane and propane was determined by sampling an equilibrium cell using chromatographic techniques. An excess of solid AOT was loaded into a 17 mL high pressure vessel. The fluid was saturated with AOT by recirculation through the solid bed of AOT using a magnetically coupled gear pump (Micropump, No. 182-356). The solution was sampled, by means of a HPLC valve having a 100 uL sample volume, to a UV absorbance detector (ISCO $V^4$) at a constant flow rate of the temperature regulated subcritical liquid. The transport fluid (or mobile phase) was pure liquid ethane or propane at 300 bar and 25° C. The amount of AOT in the 100 uL sample was determined by integrating the absorbance peaks (monitored at 230 nm) following calibration using solutions of known concentration and correction for differences in flow rate.

A high pressure vibrating tube densimeter (Mettler-Paar DMW 512) was used to measure the density of the AOT/water/supercritical ethane solutions. The temperature of the cell could be controlled to $+/-0.01°$ C. by recirculating water from a thermostated water bath through the water-jacketed measuring cell. The micelle solutions were prepared by loading measured amounts of AOT and water into a 50 mL high pressure vessel which was then placed in the water bath. After the vessel was filled with supercritical ethane, the solution was mixed and recirculated through the vibrating tube sensor by means of a magnetically coupled gear pump. The temperature and pressure were measured using the previously described instruments. The partial molal volume of AOT, $v_2$, in supercritical ethane was calculated from the expression, $$v_2 v - y_1 (dv/dy_1)_{T,P} \quad (1),$$

where v is the specific volume of the solution and y1 is the ethane mole fraction. The measured AOT concentration was converted to AOT mole fraction using an iterative procedure. Initially, the value of $v_2$ for pure AOT solid was used to estimate $y_2$, allowing a new value of $v_2$ to be calculated from which a better estimate $y_2$ of could be obtained.

Results and Discussion

A simple visual experiment in which polar dyes or proteins (that are insoluble in the pure fluid) are solubilized by supercritical fluid-surfactant solutions is convincing evidence for the existence of a reverse micelle phase. A colored azo dye, neutral red (3-amino-7-dimethylamino-2-methylphenazine hydrochloride) is very soluble in a 0.075 M AOT/supercritical ethane solution at 37° C. and 250 bar when the water-to-AOT molar ratio, W, is above 3. Similarly, supercritical propane reverse micelle solutions at 103° C. and 250 bar can solubilize substantial amounts of high molecular weight proteins such as Cytochrome-C. These polar substances were determined to have negligible solubility in the pure fluid and in the water saturated fluid. In the binary solvent of AOT and propane (where we assume W approximately=1 due to the difficulty of completely drying the AOT), these polar substances are only sparingly soluble, but by increasing W to 3 or above, the solubility of the polar compounds is greatly increased.

Solubilization of Cytochrome-C in propane/AOT/-water solutions is particularly convincing evidence for reverse micelle formation in supercritical fluids because it excludes the possibility of a simple ion-pair mechanism of solubilization. It seems likely that this large, water soluble enzyme is solvated by the highly hydrophobic fluids only if the polar functional groups on the surface of the protein are shielded from the nonpolar fluid by surfactant molecules.

A technique called dynamic light scattering (DLS) (also known as quasi-elastic light scattering) was used to directly measure micellar diffusion rates in near critical and supercritical fluids. A central element of this light scattering instrument is the high pressure, light scattering cell which contains a high precision, 2 cm diameter sapphire tube. Diffusion coefficients are determined by using the method of cumulants to analyze the autocorrelation function of the scattered light. For a solution containing water, AOT (an anionic surfactant) and ethane, the micellar diffusion coefficient varies between 1.3 and $1.8 \times 10^{-5}$ cm$^2$/sec in the range of pressure between 220 to 350 bar as shown in FIG. 20. The micelle diffusion rate also changes as a function of temperature at constant pressure as shown in FIG. 21 because the more fundamental variable, density changes substantially. The diffusion rate of a micellar structure in ethane under these conditions is 20 times higher than a comparable structure in liquid iso-octane. The hydrodynamic radii of these micellar structures, shown in FIG. 22, were calculated from the Stokes-Einstein relationship. A micelle in supercritical ethane contains an aggregate of approximately 20 surfactant molecules. The hydrodynamic radius appears to increase in supercritical ethane as pressure is reduced (37° C.) but this observation could also be interpreted as clustering of several smaller micelles. FIG. 22 clearly shows how pressure and temperature (and density) affect the micelle size or the size of the micellar cluster.

The critical micelle concentration (CMC) defines the minimum amount of surfactant required to form the reverse micelle phase, and may be considered to represent the solubility of the surfactant monomer (although the CMC for reverse micelle forming surfactants is much less clearly defined than in normal micelle systems). At surfactant concentrations well above the CMC the small amount of monomeric surfactant (and perhaps small pre-micellar surfactant aggregates) exists in equilibrium with the bulk of the surfactant in the form of micellar aggregates. For example, the CMC of AOT in liquid iso-octane is about $6 \times 10^{-4}$M.

Figure 5:
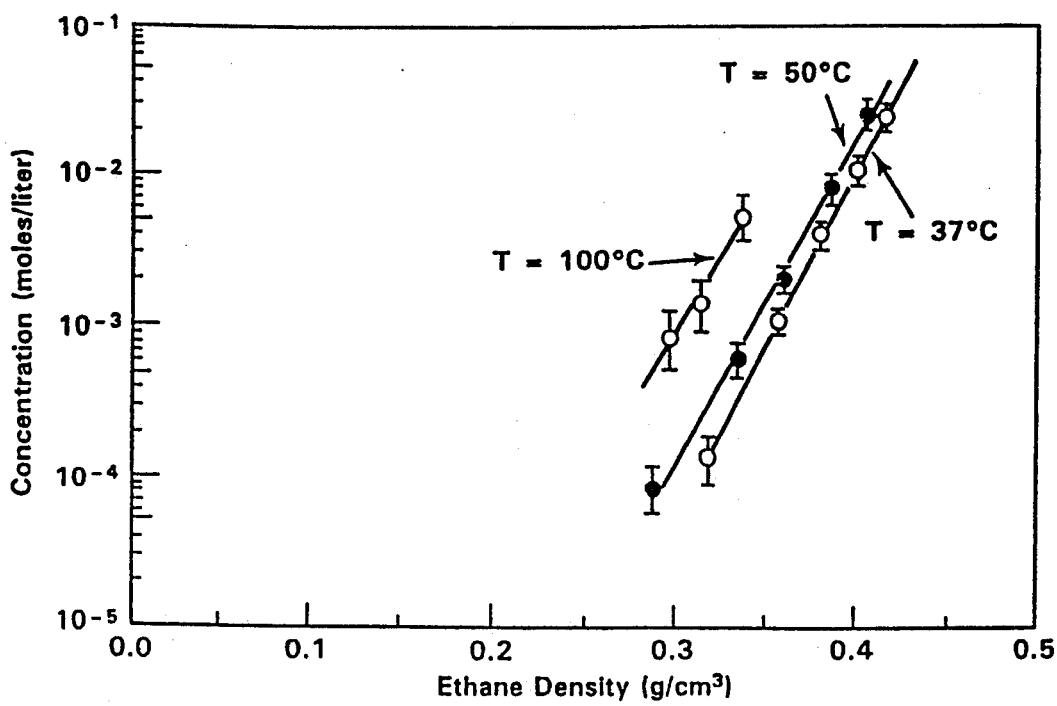
FIG. 5 is a graph of solubility of AOT in supercritical ethane at 37, 50 and 100° C., $W = 1$.
Figure 6:
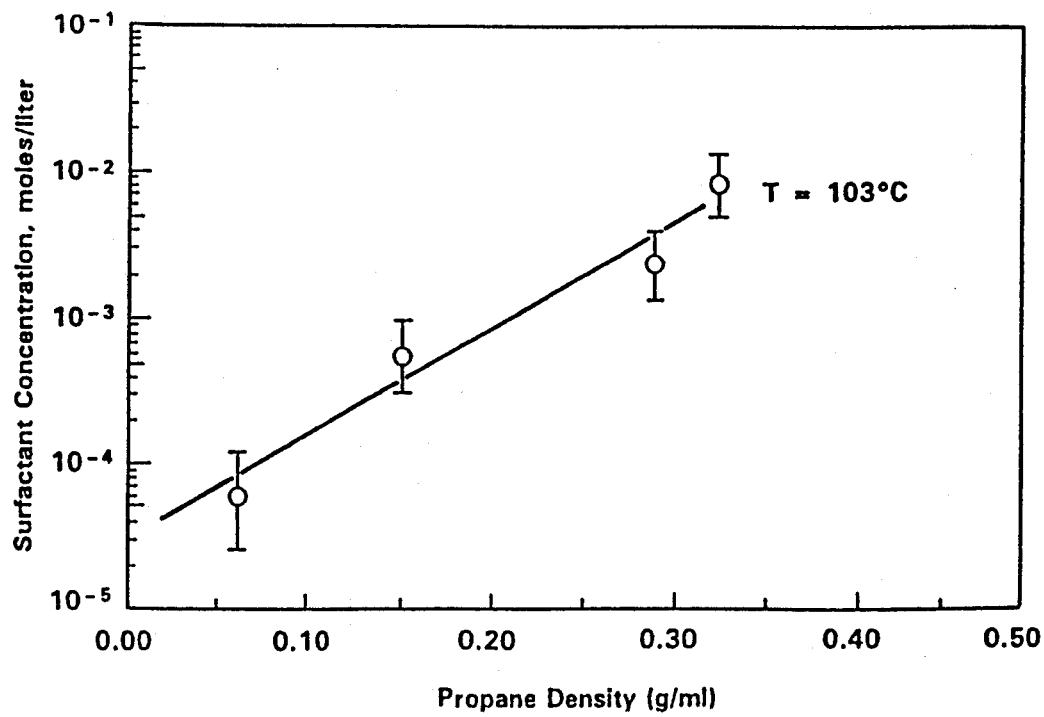
FIG. 6 is a graph of solubility of AOT in supercritical propane at 103° C., $W = 1$.

The solubility of surfactant monomer in a particular solvent is dependent on specific solvent-solute forces. The dominant intermolecular interactions between polar surfactant and alkane solvent molecules are the dipole-induced dipole and the induced dipole-induced dipole forces. In supercritical fluids, the magnitudes of these interactions are strongly dependent on the pressure and temperature of the fluid which determine the intermolecular distances (17). At similar molecular densities, hexane and iso-octane are expected to be better solvents for polar surfactant molecules since their polarizabilities ($12 \times 10^{-24}$ and $17 \times 10^{-24}$ cm$^3$, respectively) and, hence, the induced dipoles are greater than those for ethane and propane ($4.4 \times 10^{-24}$ and $6.3 \times 10^{-24}$ cm$^3$, respectively). Even so, AOT exhibits very high solubility in supercritical ethane and propane at moderate densities as shown in FIGS. 5 and 6. For ethane, the solubility is much higher than one would expect for a high molecular weight, polar molecule in a low molecular weight fluid. This high solubility is readily explained in terms of formation of AOT aggregates, i.e., a reverse micelle phase dispersed in the fluid.

It also seems likely that at moderate pressures the surfactant has a solubility above the CMC in ethane and propane, although the data show no evidence of changes in solubility dependence upon density due to a CMC. As indicated in FIGS. 5 and 6, there is a nearly linear relationship between log[AOT] solubility and fluid density over several orders of magnitude of AOT concentration. This type of behavior would be expected for the solubility of a non-aggregate forming, solid substance in a supercritical fluid (12). The solubility and phase behavior of solid/supercritical fluid systems has been described by Schneider (18) and others, and such behavior can be reasonably well predicted from a simple Van der Waal's equation of state. Clearly, this approach is not appropriate for predicting surfactant solubilities in fluids since it does not account for the formation of aggregates or their solubilization in a supercritical fluid phase.

In FIGS. 5 and 6, one might expect to see two different solubility regions. At low fluid densities, where intermolecular forces are reduced and the surfactant concentration is below the CMC, the solubility should increase gradually as the density increases. At higher densities, above the CMC, the solubility might be expected to increase more rapidly because the total surfactant solubility is dominated by the saturation concentration of micelles in the fluid. This type of behavior is not apparent in FIGS. 5 and 6, perhaps because the CMC is below $10^{-4}$M.

An alternative explanation is that the CMC for AOT in supercritical fluids is strongly density dependent. This might be expected because the CMC can be sensitive to temperature and the nature of the continuous phase. As we have noted, at high dilution there is typically a nearly linear relationship between log [solubility] and fluid density for solid solutes. If the AOT monomer conforms to this behavior, the CMC might be expected to have a similar relationship with fluid density i.e., log (CMC) is proportional to density. Further studies are required to resolve these points.

The effect of temperature on AOT solubility in ethane is also shown in FIG. 5. The range of fluid densities studied was limited at higher temperatures by the pressure constraints of our apparatus. In our initial correspondence it was shown that the minimum ethane density necessary to support reverse micelles (at W approximately = 1) had a nearly linear inverse relationship with temperature extending from the near-critical liquid (at 23° C.) to well into the supercritical region (>100° C.). (The previous experiments utilized an AOT concentration of about $2 \times 10^{-2}$ moles/liter, and correspond to a solubility measurement in which the fluid density necessary for solvation at a given temperature is determined. The results are in good agreement with the present more extensive measurements obtained using a completely different method.) The solubility of AOT is greater in propane than in ethane at similar temperatures, although the greater slope of the log [AOT] vs. density data for ethane suggests that the differences are small at higher densities.

Figure 7:
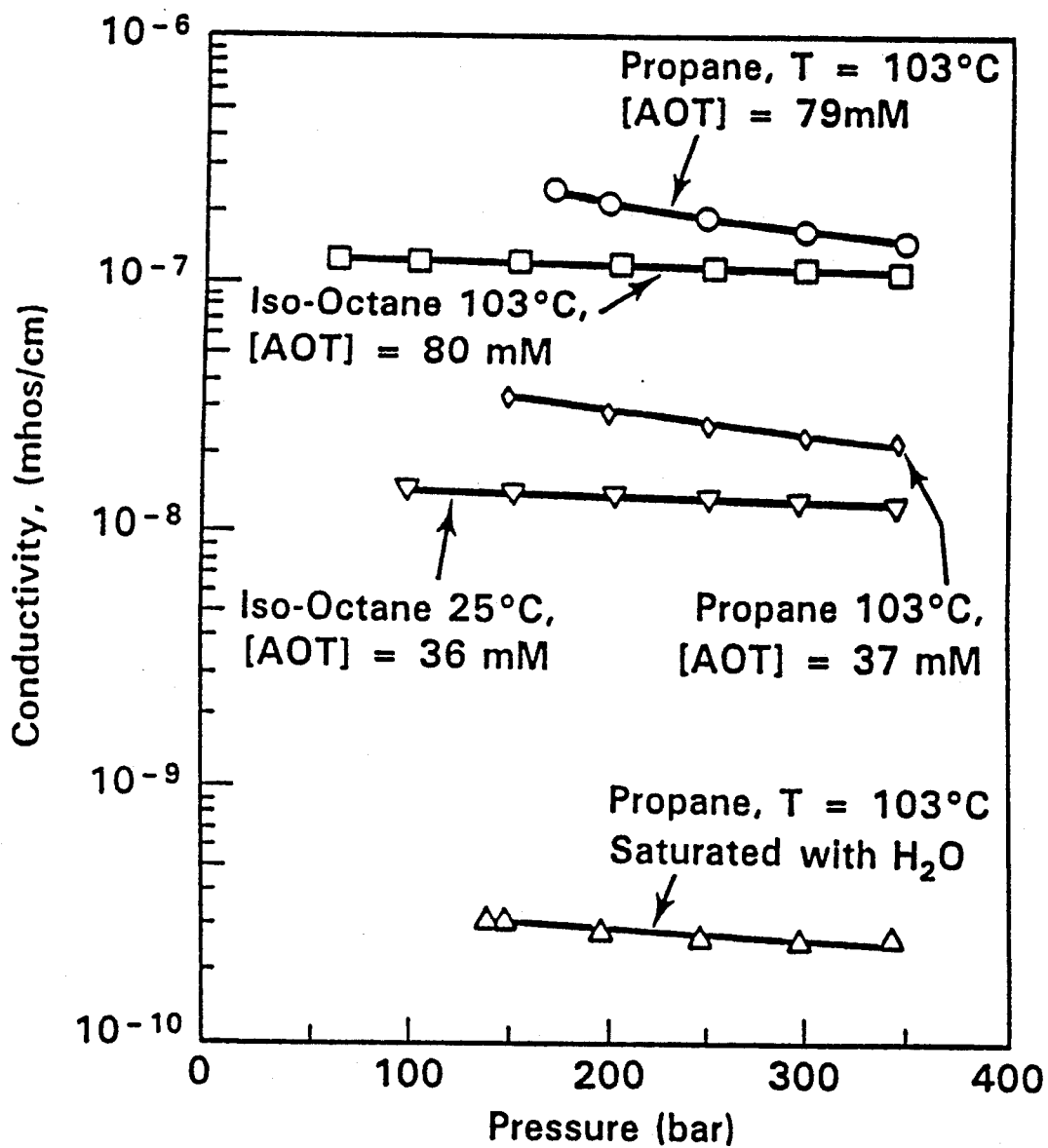
FIG. 7 is a graph of conductivity of reverse micelle phases in supercritical propane and liquid iso-octane at various pressures, $W = 1$.

FIG. 7 gives the conductivities of solutions containing reverse micelles in supercritical propane at 103° C. for pressures from 75 to 350 bar. The AOT concentrations in these solutions were approximately 37 and 80 mM at W approximately = 1. In all cases the conductivities of these solutions are below $10^{-6}$ mhos/cm, which is consistent with a reverse micelle structure in a nonpolar fluid. Reverse micelle solutions formed in supercritical propane are more conductive than those formed in liquid iso-octane at the same temperature, pressure, and AOT (and water) concentrations. Part of this difference can be explained by the higher mobility of ions in the lower viscosity propane. The viscosity of propane at 103° C. varies from 0.07 cp to 0.09 cp between 175 to 350 bars, whereas the viscosity of iso-octane is 0.5 cp at these conditions. For the supercritical propane solutions, conductivity decreases at higher pressure because of reduced ionic mobility as the viscosity of the fluid increases. However, the difference in measured conductivity between propane and iso-octane solutions at 103° C. is not as large as would be expected based solely on the factor-of-six difference in viscosity of the two fluids. This indicates that other factors, such as differences in the concentration of surfactant monomer, may be important.

As shown in FIG. 7, adding surfactant to propane increases the conductivity by several orders of magnitude over the binary system of propane saturated with pure water. The predominant contribution to conductance in these solutions is anticipated to be from disassociated surfactant monomer in the continuous phase or from micelles containing one or more ionized molecules. In either case the degree of dissociation is quite low, but should be slightly higher in the liquid alkane solutions due to the somewhat larger dielectric constant.

Measurements of supercritical ethane density versus the AOT concentration shown in FIG. 8 (T=37° C., P=250 bar) indicate that the properties of the supercritical continuous phase resemble those of the pure fluid. The dispersed micelle phase does not appear to increase the critical temperature or critical pressure of the binary solution to the point of inducing a phase change in the system. There is a small increase in density as surfactant is added to the system which confirms the visual observation that a second liquid phase of much higher density is not formed.

From the data in FIG. 8, the partial molal volume of an AOT molecule in a micellar aggregate dispersed in supercritical ethane at 37° C. and 250 bar is estimated to be $-43 +/-55$ cc/mole. A negative partial molal volume for a solute in a supercritical fluid is not surprising since lower molecular weight solutes, such as naphthalene in ethylene, near the critical point can have a partial molal volume of $-3000$ cc/mole (19). This behavior is due to the locally higher solvent density around the higher molecular weight, polarizable solute molecule (15, 19). The partial molal volume of AOT in ethane is consistent with a micellar structure surrounded by a dense, liquid-like ethane shell dispersed in the continuous, supercritical ethane phase.

The pressure dependence of the phase behavior of these supercritical n-alkane solutions containing a reverse micelle phase is striking and can be illustrated by a description of the solvation process from view cell studies. The dissolution of 1 g of AOT solid (W approximately = 1) into 25 mL of supercritical ethane or propane proceeds in four distinct stages. At low pressures the AOT solid is in equilibrium with a low density fluid containing a small or negligible amount of dissolved solid. At somewhat higher pressures (80 to 106 bar) the AOT begins to "melt," forming a system with three phases: solid AOT, a viscous AOT liquid with a small amount of dissolved fluid, and a fluid phase containing dissolved surfactant. At moderate pressures a two-phase system exists consisting of a viscous, predominantly AOT liquid in equilibrium with a fluid containing appreciable amounts of surfactant. Finally, at high pressures (typically >120 bar) a single, reverse-micelle containing phase is created with the AOT completely solvated by the fluid.

Figure 10:
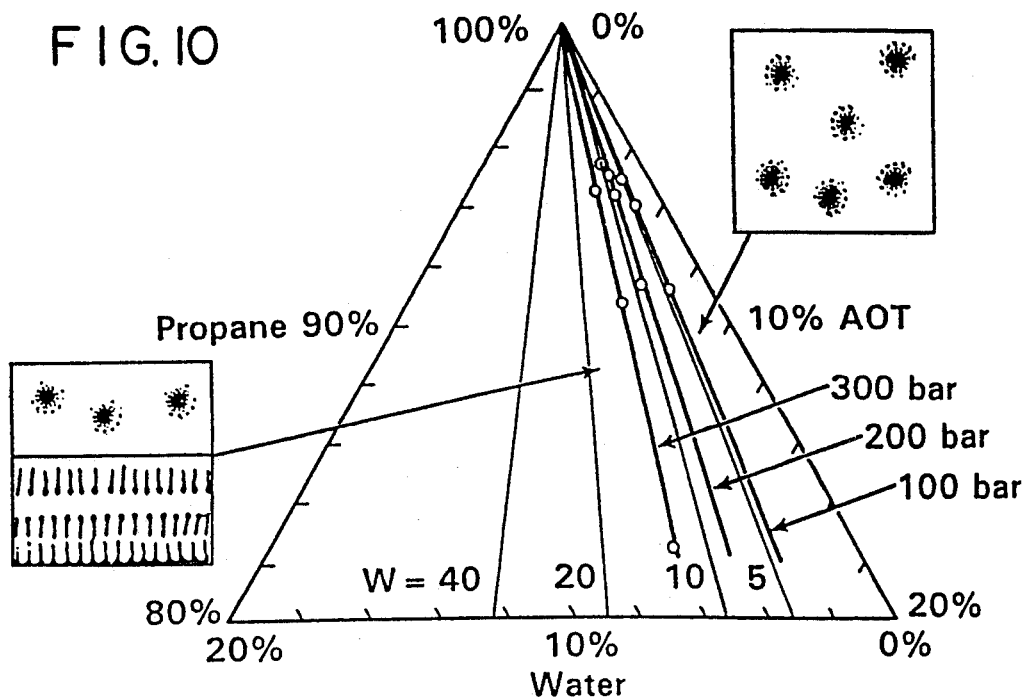
FIG. 10 is an enlargement of FIG. 2(d) showing the propane-rich corner of the propane/AOT/water ternary phase diagram (weight %) at 103° C. and at three pressures, 100, 200 and 300 bar.
Figure 11:
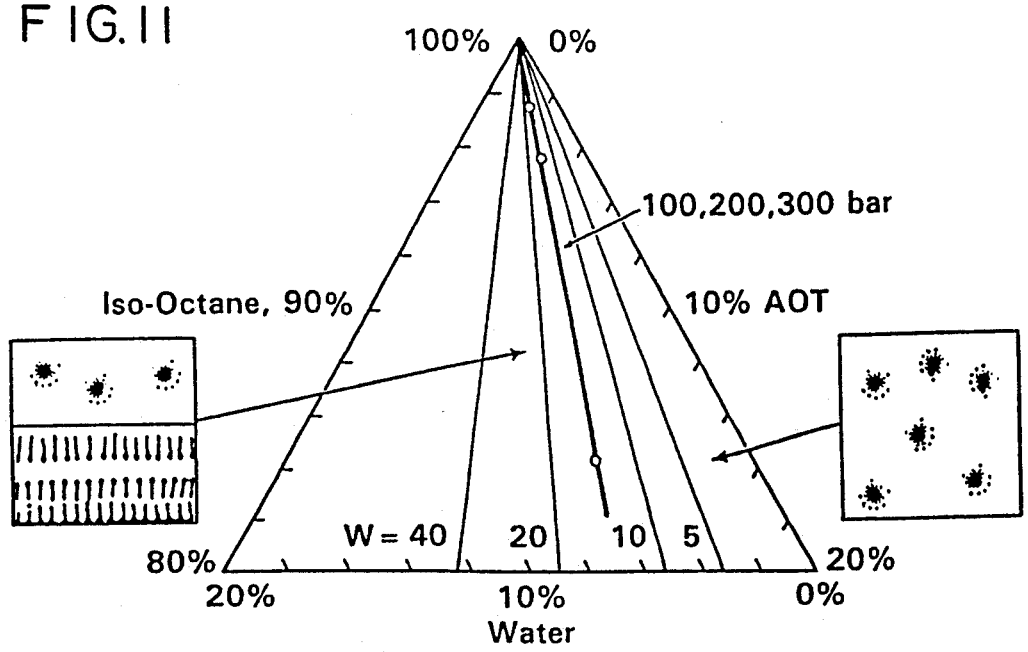
FIG. 11 is an enlargement of FIG. 2(f) showing the iso-octane rich corner of the iso-octane/AOT/water ternary phase diagram (weight %) at 103° C. and at three pressures, 100, 200 and 300 bar.

The ternary phase diagrams for supercritical ethane, propane and liquid iso-octane surfactant solutions are shown enlarged in FIGS. 9, 10 and 11. The region of interest in this study is the alkane rich corner of the phase diagram representing 80 to 100% alkane and less than 10% water by weight. Each diagram shows the location of the phase boundaries separating the single - and two-phase regions at several different pressures in the range of 100 to 350 bar. The areas to the right of these boundaries are regions where a single, dispersed droplet (micelle or microemulsion) phase exists; to the left of these lines, a two-phase system exists containing a liquid and a dense gas (or near critical fluid) phase. The liquid phase is predominantly water containing some dissolved surfactant which is most likely in the form of monomer or normal micelle aggregates. The phase boundary lines also define the maximum water-to-surfactant ratio, $W_o$. At a given pressure, $W_o$ appears to be nearly constant over the range of AOT concentrations studied. The supercritical ethane data were obtained at 5° C. above the ethane critical temperature; the supercritical propane data are at the same reduced temperature ($T/T_c$) as the ethane (6° C. above the critical temperature of propane). To compare the phase behavior of a liquid alkane with that of supercritical propane, the phase diagram for liquid iso-octane at 103° C. and various pressures is shown in FIG. 11.

The phase boundary lines for supercritical ethane at 250 and 350 bar are shown in FIG. 9. Since the surfactant was only slightly soluble below 200 bar at 37° C., the study of ternary phase behavior was restricted to higher pressures where the AOT/ethane binary system is a single phase. As pressure is increased, more water is solubilized in the micelle core, forming larger micelles in the supercritical fluid continuous phase. The maximum amount of water solubilized in the supercritical ethane reverse micelle-phase at moderate pressures is relatively low, reaching a $W_o$ value of 4 at 350 bar.

In contrast to ethane, the maximum amount of solubilized water in the supercritical propane reverse micelle system at similar pressures much higher, having a $W_o$ value of 12 at 300 bar and 103° C. Again, the $W_o$ values increase with pressure from a $W_o$ value of 4 at 100 bar to $W_o=12$ at 300 bar, as shown in FIG. 10. The phase behavior in these supercritical fluid systems is markedly different than that in the liquid iso-octane reverse micelle system. In the liquid iso-octane system, shown in FIG. 11, there is no substantial effect of pressure on the phase behavior at the temperature studied.

The upper phase is consistent with that of a reverse micelle or dispersed microemulsion droplet structure, although uncertainty remains regarding the shape and size distribution of these structures. The lower liquid phases for these systems have not yet been characterized but we expect that they contain predominantly water with dissolved monomer or normal micelle aggregates. The association of amphiphilic species in liquid systems produces a multitude of possible microstructures which include liquid crystalline phases, normal micelle phases, bicontinuous structures, pre-micellar aggregates as well as two different reverse micelle or microemulsion containing phases in equilibrium. Although much progress has been made (20), thermodynamic models of phase behavior in liquid systems and detailed understanding of their structures is incomplete. We can, however, qualitatively describe the observed phase behavior of microemulsions formed in supercritical fluids.

To assess the importance of specific forces, it is convenient to describe the total free energy of a component in the microemulsion as being comprised of the sum of the contributions from distinct classes of intermolecular forces (21) (e.g., Coulombic, Van der Waals, etc.). The derivative of the total free energy is equal to the chemical potential of a component. From this we can determine the chemical equilibrium of two or more phases since the chemical potentials of a component in each phase are equal. One important constraint on the component free energy is the surfactant packing geometry, as has been described by Mitchell and Ninham (22). In this packing geometry model, the curvature of the interfacial surface is determined by the volume of the hydrocarbon tails of the surfactant as well as the surface area of the polar head groups. This approach may qualitatively describe the decrease in the maximum amount of solubilized water in short chain length alkane-micelle solutions. The greater penetration of the surfactant tails by propane or ethane, and the greater volume of these tails compared with that in liquid hydrocarbon solvents, may result in an interfacial surfactant layer with higher curvature, thus allowing only smaller reverse micelles.

There are other contributions to the free energy of a component in a microemulsion which are important as well. Inside the reverse micelle, Coulombic forces of the ionic headgroups dominate the structural considerations (21). These Coulombic forces are expected to be of similar magnitude in both supercritical fluid and a liquid is the free energy of mixing of the micelles into the continuous phase. However, an important distinction between a supercritical fluid and a liquid is the free energy of mixing of the micelles into the continuous phase. In the variable density supercritical fluid, the free energy of mixing varies considerably with pressure, in contrast to liquid systems where there is relatively little change. It then seems possible that the strong electrostatic contributions to the free energy determine the allowable size of the micelle, and that the solubility of these distinct species is predominantly determined by the free energy of mixing in the fluid phase. In simpler terms, larger micelles can only be solvated by fluids which have higher densities.

Supercritical Fluid Reverse Micelle Chromatography

Polar compounds in aqueous systems have been observed to partition into nonpolar solvents containing reverse micelles, forming the basis for alternative extraction and separation methods (3). Ionic species and highly polar water-soluble compounds, including proteins, have been solubilized in nonpolar solvents containing reverse micelles such as hexane (3). Specific solvation effects involving reverse micelles in liquids have been elucidated, showing that solvation may occur in the center water pool or at the surfactant-water interface (24, 31, 32). Selectivity may be influenced by control of the reverse micelle structure, varying concentration of surfactant and water to surfactant ratio W ($[H_2O]/[\text{surfactant}]$), and by adjusting pH or ionic strength (8, 33–36).

Applications of micelles in analytical separations have recently been reviewed (37, 38), and the use of reverse micelle mobile phases in normal-phase liquid chromatography has been reported (7).

Normal micelle liquid mobile phases have been investigated (35, 36), with the aim of providing improved separation of less polar species by reversed phase liquid chromatography. By analogy, reverse micelle mobile phases would allow the separation of more polar species by normal phase liquid chromatography. In principle, normal-phase HPLC would frequently be the method of choice for separation of polar compounds. That it is not often used has been discussed by Caude et al. (39–41), who describe problems with reproducibility over time. Dorsey and workers (7) have further studied the difficulties with reproducibility of normal-phase HPLC caused by mobile phase water impurities and demonstrated improvements utilizing reverse micelle containing mobile phases. Other advantages of micelle chromatography include eliminating the time for column reequilibration at the end of a gradient (42, 43). Solubility of proteins and complex biological matrices in reverse micelle systems enables injection of complex samples without prior separations (44, 45). Use of reverse micelles consisting of phosphatidylcholilne may also offer an alternate means of mimicking lipid partitioning for determining lipophilicity in a manner similar to, yet much simpler than, emulsion pseudophase liquid chromatography (46). Information about micelle structure, ionic strength, and acid-base behavior can be obtained by investigating the effects of secondary chemical equilibria on separations (4, 47, 48).

To date supercritical fluid chromatography (SFC) has relied on polar fluids or binary mixtures containing a polar modifier to increase the polarity of the mobile phase and allow separation of more polar compounds (49, 50). Relatively high critical temperatures of more polar fluids and fluid mixtures containing more than a few percent modifier can limit their application to less polar or labile compounds. Reactivity of some of the polar fluids (i.e., $H_2O$, NH) at supercritical conditions, and related experimental complications, further hinders their use.

Reverse micelle formation in supercritical solvents with low critical temperatures introduces another means of modifying the mobile phase in SFC. Though complex in their phase behavior, supercritical reverse micelle mobile phases offer an alternative to polar and modified fluids and are capable of solvating large molecules such as Cytochrome-C in a nonpolar supercritical fluid. Mobile phases incorporating reverse micelles should offer other advantages for SFC, where two additional variables for controlling micelle phase behavior become available: temperature and pressure (or density). Reverse micelle SFC should also benefit from the enhanced diffusion rates and lower viscosities of such mobile phases. Following are the results of combining the solvating power of reverse micelles with supercritical mobile phases for chromatographic separations.

Experimental Section

Materials

The following materials were used as received: Aerosol OT or AOT [sodium bis(2-ethylhexyl)sulfosuccinate (Aldrich]), phenol, 2-naphthol, and resorcinol (J. T. Baker), HPLC grade n-hexane (Burdick & Jackson), CP grade propane (Linde).

Equipment

Samples were injected with a 200-nL injection volume valve (Cl4W, Valco) onto a silica microbore column (Spheri-5, 5 um, 1 mm×250 mm, Brownlee Labs) maintained at constant temperature ($+/-0.2°$ C.) in a gas chromatographic oven (Model 5890, Hewlett-Packard). A syringe pump (Model 8500, Varian Associates) was used to deliver the mobile phase at constant pressure ($+/-0.2$ bar) or constant flow rate ($+/-5$ uL/h). Column effluent was monitored with a variable wavelength UV detector (Model V4, Isco) operated at 254 nm, utilizing 200 um i.d. fused-silica capillary tubing for the absorption cell.

Procedure

The pressure differential across the column was <30 bar at the flow rates used in this study. A short length of 24 um i.d. capillary tubing served as a flow restrictor, maintaining an average pressure of approximately 250 bar in the analytical column for the selected flow rate.

The hexane reverse micelle mobile phase was prepared by dissolving the appropriate weight of AOT ($5\times10^{-2}$M) in hexane and adding water (Milli-Q system Millipore) to provide a W ([$H_2O$]/[AOT]) of 5.0. Preparation of the propane reverse micelle mobile phase was accomplished by adding AOT and water to the syringe pump, filling the syringe with liquid propane, pressurizing the system to 250 bar, and mixing with a small magnetically coupled pump (Micro Pump).

The maximum water to surfactant ratio, $W_o$, defines the maximum size of the water core of the reverse micelles; larger amounts of water result in formation of a two-phase system. Studies of the effect of pressure on $W_o$ solubilized in the supercritical propane-AOT-water system were performed with a high-pressure, temperature-regulated view cell (volume approximately 20 mL) with a magnetically coupled stirrer (Model 200, VWR). The AOT was weighed and introduced into the cell, and propane was introduced with a syringe pump (Model 8500, Varian Associates). Water was added via a hand-operated high-pressure pump (Model 86-6-5, High Pressure Equipment), and the phase behavior was followed visually allowing 10 min for equilibration.

Results and Discussion

Reverse micelle mobile phases for SFC can be utilized over a broad range of conditions. Dissolution of AOT (at low water concentrations) occurs in three stages as the fluid density increases. At low fluid densities three phases exist: solid AOT, a viscous AOT-propane liquid mixture, and a gaseous upper phase. At intermediate densities an AOT-liquid propane phase exists in equilibrium with a predominantly gaseous propane upper phase. Finally, at higher densities a single micelle-containing phase is formed. As water is added to this phase, the micelles are "swollen," altering their solvating properties. Supporting data has been previously published in Gale, R. W., Fulton, J. L., and Smith, R. D., "Reverse Micelle Supercritical Fluid Chromatography," Anal. Chem. 1987, 59, 1977–1979, below referenced as Tables I, II, and III.

As the density (pressure) of the solution is reduced, a sharp phase-transition occurs with precipitation of a second aqueous-containing phase and the apparent destruction of the micelle phase. The maximum water to surfactant ratio ($W_o$) for the ternary system was found to decrease with increasing temperature and to increase with increasing pressure or density (Table I). It has previously been observed that the water content of the micelle partially determines their solvating ability (1,2). Control of $W_o$ by pressure variation in a supercritical or near critical reverse micelle system provides a means for manipulating the solvating power of the mobile phase. Addition of salts or polar solutes can also alter $W_o$. Solubility in the bulk (continuous) supercritical fluid phase is also controlled by pressure, increasing the potential utility of this approach.

Figure 12:
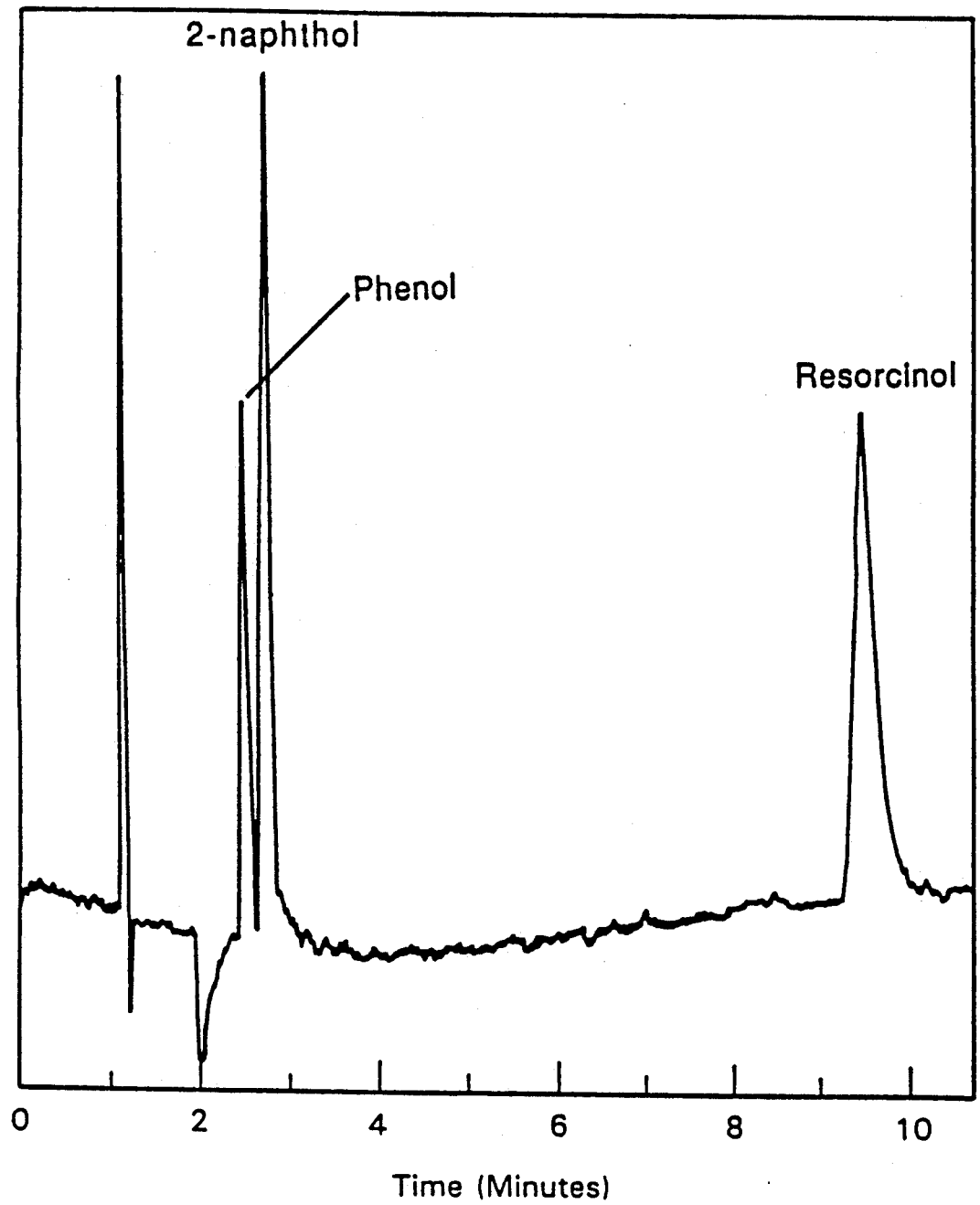
FIG. 12 is a normal-phase reverse micelle supercritical propane chromatogram: propane 110° C., 250 bar; [AOT] = $5 \times 10^{-2}$ M, $W = 5.0$. Peak identification is as follows: (A) phenol, (B) 2-naphthol, (C) resorcinol.

In these initial studies using a reverse micelle mobile phase in SFC, retention and separation efficiency were compared with a pure supercritical mobile phase and to both the pure subcritical liquid and the liquid reverse micelle mobile phases at the same temperature. Retention data for the three model compounds for the various mobile phases at 25° and 110° C. are given in Table II. FIG. 12 shows a chromatogram obtained for the test mixture using a reverse micelle supercritical mobile phase.

At constant temperature, the capacity factor (k') was found to decrease substantially for all solutes when the pure solvent mobile phase was replaced by a reverse micelle mobile phase with the same solvent. Although the solvent strength of liquid propane is much less than n-hexane (k' in propane was greater than 100 for all three analytes), the reverse micelle mobile phases of both solvents gave similar retention at 25° C. This suggests the major effect is due to the presence of the reverse micelles or the surfactant (51, 52). Phenol and substituted phenols are known to partition into AOT reverse micelles (53). It should also be noted that at 25° C. the retentions of phenol and 2-naphthol are reversed upon going from pure to reverse micelle solvents. Such behavior suggests that 2-naphthol partitions to a greater extent into the reverse micelles than phenol.

Solute retention (Table II) for the pure solvent mobile phases decreased by a smaller amount, and retention of resorcinol increased slightly with increasing temperature. The latter was unexpected based solely on an adsorption retention mechanism. It remains to be determined whether a shift in the critical micelle concentration (or W) in going from 25° to 110° C. could account for such behavior (which could be selective in the effect upon retention depending upon the location of solute partitioning). Two processes have been described as influencing retention under such conditions: coverage of active sites on silica (silanol groups) with a polar or ionic species such as AOT (7, 54) and solute partitioning between the mobile phase solvent and reverse micelles. Large changes in retention were previously reported at AOT concentrations below the critical micelle concentration (7). Equilibrium between free and surface adsorbed micelles may also play an important role, though the dynamics of micelle adsorption on surfaces are not well understood. Alternatively, a shift in the $pK_a$ of resorcinol at the higher temperature, which would effect partitioning into the micelles, may also explain the observations.

The chromatographic efficiency of supercritical reverse micelle mobile phases was also studied and found to decrease for both liquid and supercritical micelle systems as compared with pure solvents as expected. Dorsey et al. (7) reported that efficiency decreased for liquid mobile phases that contained reverse micelles and attributed this to the slow rate of solute partitioning into and out of the micelle phase. Efficiency reduction in micelle systems can also be attributed to the much lower diffusion rates of the solute contained in a micelle compared to free solute in a pure mobile phase. Light scattering studies have shown that there is often an optimum pressure which leads to the highest micelle diffusion rates at a given temperature. This arises due to the opposing influences of fluid diffusivities (greatest at low pressures) and minimization of micelle clustering (which is minimized at conditions which are most removed from the conditions for phase separation. As shown in Table III, efficiency generally increased with temperature (although efficiency for phenol in pure hexane actually declined). It should be noted that the efficiencies indicated in Table III would be somewhat reduced if the peak asymmetry apparent in FIG. 12 was more rigorously considered (55); however, the relative efficiencies given would remain essentially unchanged.

Increases in efficiency are expected by operating above the fluid (continuous phase) critical temperature and at moderate fluid densities because of higher diffusion rates and lower fluid viscosities (49, 56). One reason that reverse micelle chromatography may be better adapted to supercritical fluids is that this gain in efficiency at higher temperatures tends to minimize the loss in efficiency due to the use of micelle systems. The higher diffusion rates and lower viscosities of supercritical fluids, compared to those of liquids at the same temperature, may enhance micelle diffusion rates leading to an increased overall efficiency.

Normal phase reverse micelle supercritical fluid chromatography has been demonstrated and a preliminary study of temperature effects on reverse micelle mobile phases has been made. The results show that retention times of polar solutes are substantially reduced by using a micellar mobile phase and that solutes which are more polar can be separated. The higher efficiencies obtained by using a reverse micelle supercritical fluid mobile phase are more representative of pure fluid systems than liquid micelle phases. The effect of pressure on retention remains to be examined for reverse micelle supercritical fluid systems. It is anticipated that selectivity may be adjusted by using PH, ionic strength, or supercritical fluid pressure to control solute-micelle partitioning, similar in manner to that used in controlling selectivity in extraction processes for separating amino acids and proteins (3, 8, 34). Chromatography with reverse micelles, while more complex than using pure liquids or fluids, decreases retention times for polar solutes with silica stationary phases. The extension of supercritical reverse micelle phases to capillary columns should provide enhanced efficiencies. Larger scale process separations using packed columns should be particularly attractive.

The effects of pressure, the water-to-surfactant ratio, W, and surfactant concentration extend the use of these new mobile phases.

The manipulation of pressure and/or W for a reverse micelle system provides a method to change the solvating power of the mobile phase. Specific solvation effects involving reverse micelles in liquids have been elucidated, showing that solvation may occur in the center water pool or at the surfactant-water interface (6, 25, 26). Selectivity may be influenced by control of the reverse micelle structure, varying concentration of surfactant and water-to-surfactant ratio (W), as well as by adjusting pH or ionic strength (4, 6).

Reverse micelle mobile phases for SFC can be utilized over a broad range of conditions. The fact that the water content of the micelles partially determines their solvating ability suggests that control of $W_o$ by pressure variation could provide a means for manipulating the solvating power of the mobile phase. Addition of salts, polar solutes or co-surfactants can also alter $W_o$. Solubility in the bulk (continuous) supercritical fluid phase is also controlled by pressure, increasing the potential utility of this approach.

Figure 13:
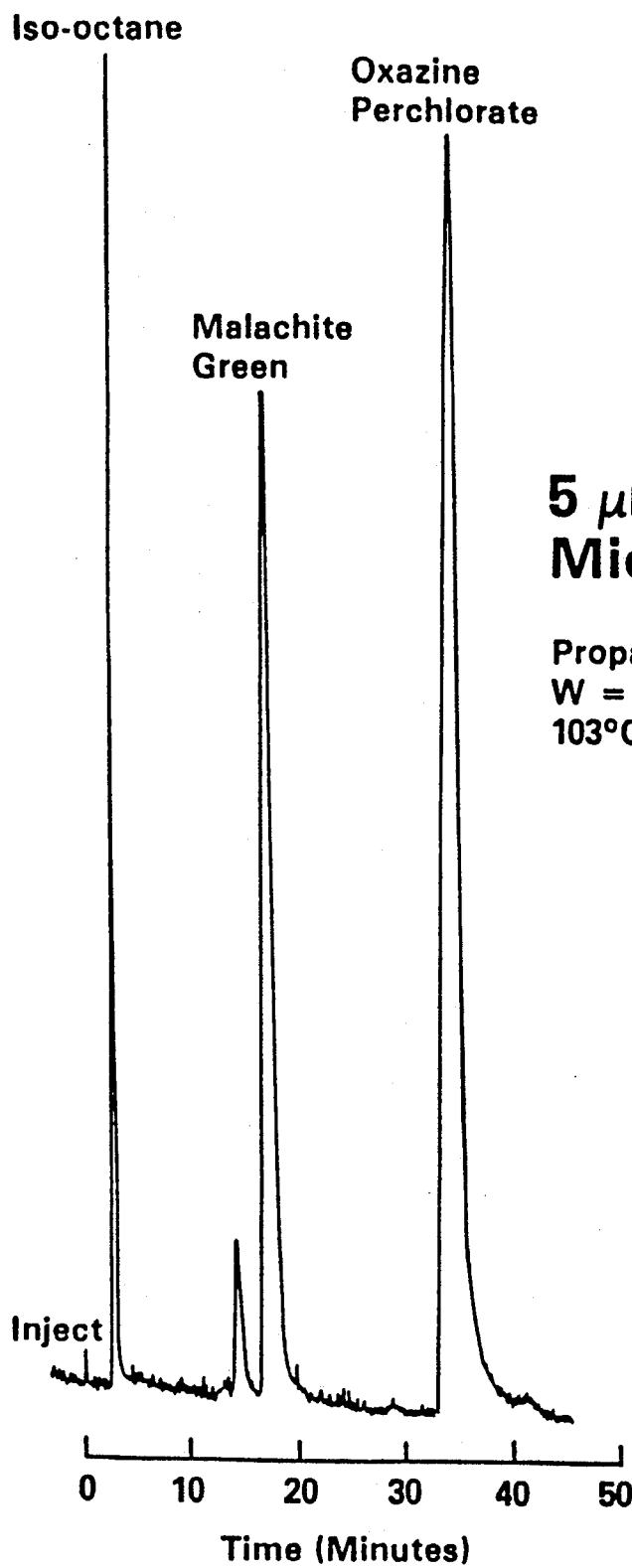
FIG. 13 is another chromatogram showing separation of two polar dyes: propane 103° C., 375 bar; [AOT] = $5 \times 10^{-2}$M, $W = 10$. Peak identification is (A)

While the studies discussed above provide useful insight into the nature of reverse micelle mobile phases, the value of reverse micelle SFC is based upon its applicability to previously intractable (at least by SFC or GC) hydrophilic compounds. An example of such an application is shown in FIG. 13, which shows reverse micelle supercritical fluid chromatography of a mixture containing two highly polar water soluble dyes (malachite green and oxazine perchlorate). In this case a solution of $5 \times 10^{-2}$M AOT with $W = 10$ in propane at 103° C. and 375 bar was used as the mobile phase. The chromatographic column was the same $C_{18}$ microbore column used for the previous studies. The sample was injected in a reverse micelle solution using liquid iso-octane as the continuous phase. The two components were also well separated from the iso-octane peak and studies at various W values showed that retention and selectivity could be varied over a wide range. To our knowledge the compounds addressed in FIG. 13 could not be solvated using nonpolar liquids or conventional pure or binary supercritical mobile phases. The potential exists to extend tremendously the range of applicability of SFC using reverse micelle mobile phases.

For chromatographic applications, results have shown that retention times of polar solutes are substantially reduced using a micellar mobile phase, allowing more polar solutes to be separated with SFC. The higher efficiencies obtained using a reverse micelle supercritical fluid mobile phase are more representative of pure fluid systems than of liquid reverse micelle phases.

Reverse micelle supercritical fluid solvents also offer similar potential advantages in a variety of extraction and separation processes. Selectivity may be adjusted using pH, ionic strength, or supercritical fluid pressure to control solute-micelle partitioning, similar in manner to that used in controlling selectivity in extraction processes for separating amino acids and proteins in liquid systems (3, 4, 6).

Extractions with Reverse Micelle Supercritical Fluid Solvents

The use of reverse micelle supercritical fluid solvents has been qualitatively explored for extraction of polar compounds from aqueous solvents. For instance, at 110° C. and 250 bar a polar dye (Basic Red No. 5) can be extracted from an aqueous phase with a supercritical propane-reverse micelle solutions (50 mN as shown in FIG. 18. The extraction efficiency is strongly dependent on pressure and there is a threshold pressure (250 bar) where the extraction efficiency increases abruptly. In addition to pressure, both pH and ionic strength effect the partitioning of a polar solute between the two phases. It also appears that increasing the overall volume fraction of the aqueous phase decreases the extraction efficiency.

This research also clearly demonstrated that high molecular weight proteins can be extracted from an aqueous solution using a reverse micelle solution containing near-critical liquid propane and a surfactant (AOT). This is a model system representative of a much broader class of systems which may involve other surfactants, cosurfactants, other fluids or fluid mixtures, more complex phase behavior and application to separation of a wide range of chemical and biological compounds. In addition, the partitioning of the protein between the aqueous phase and the liquid propane-reverse micelle phase (at 25° C.) is strongly dependent on pressure; a behavior which appears to be unique to a near-critical point liquid. The partitioning of Cytochrome-C (MW = 12,384) into the propane-reverse micelle phase occurs abruptly at 225 bar and at 275 bar extraction efficiencies approaching 100% were obtained. The results also strongly suggest that the selectivity for a specific protein in an aqueous protein mixture can be controlled with the system pressure. This propane-reverse micelle extraction technique appears to have advantages which would greatly simplify protein recovery in industrial processes.

The partitioning behavior of three different proteins [Cytochrome-C (Mw = 12,384), hemoglobin (MW = 65,600), myoglobin (MW = 18,800] and a polar dye (neutral red) were each studied separately by directly measuring protein concentration in the propane-reverse micelle phase using a UV-vis spectrophotometer equipped with a high pressure cell. In addition to pressure, both pH and ionic strength are variables which affect protein partitioning and, therefore, an initial step in characterizing this separation technique was to determine favorable pH and ionic strengths. A quick screening of three levels of pH and ionic strength using a liquid pentane reverse micelle system was used to identify favorable pH and ionic strength. For all three proteins and the dye, high extraction efficiencies were obtained with a buffered aqueous phase at pH 7 and a [Na+] = 0.1M concentration. All the propane-reverse micelle extractions were conducted at these conditions.

At higher pressures, the propane-reverse micelle systems showed strong absorbance below 300 nm (presumably scattering from near micron-sized microemulsion structures) and, hence, only proteins with visible absorbance spectra could be examined using this technique. We were also limited using this technique to studying extractions of each protein separately because the extracts had similar absorbance spectra (absorbance maximum at 408 nm). However, since each micelle contains only one protein molecule the mixture should clearly behave in the same manner as the individual components.

The extraction efficiency of Cytochrome-C and the red dye approaches 100%. At 225 bar the selectivity for Cytochrome-C versus the hemoglobin appears to be very favorable. FIG. 19 shows solubilized of water and another polar dye, malachite green, in a reverse micelle supercritical ethane and AOT solution.

Figure 3:
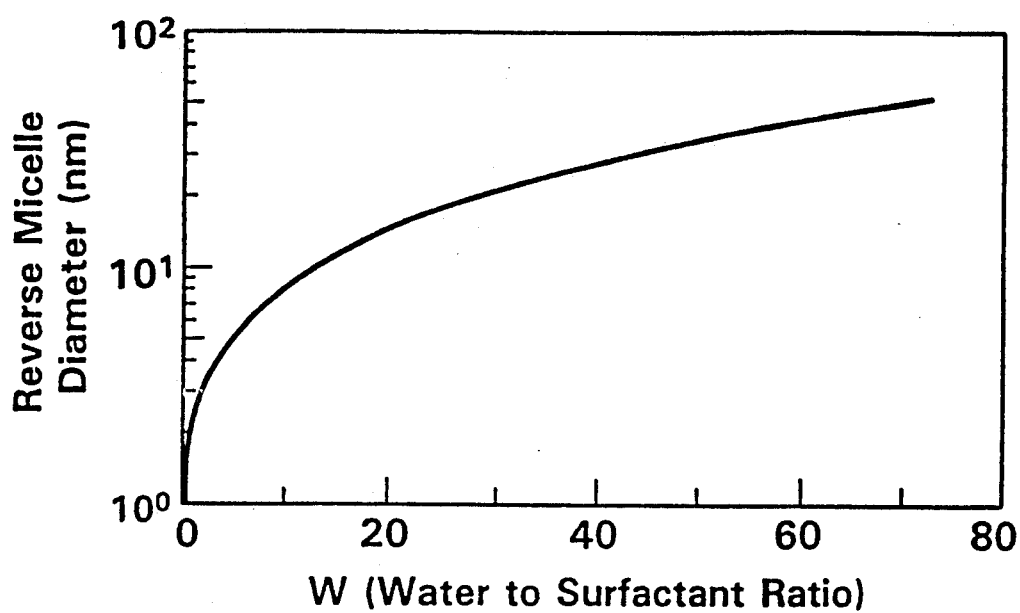
FIG. 3 is a graph of water to surfactant ratio (W) v. reverse micelle diameter.

One basis of the separation process is the fact that the maximum water to surfactant ratio, $W_o$, is determined by (or alternatively, determines) the location of the phase boundary, or $W_o$. Thus, $W_o$ can be moved. Since the water to surfactant ratio is related to reverse micelle size (see FIG. 3), the change in density effects the solvating power of the micelles. In other words, changes in density effect the ability of reverse micelles to uptake (or "encapsulate", in a or extract specific compounds. Thus, selectivity arises from both changes in size and their solvent characteristics. For $W_o < 10$ the core resembles an ionic fluid and is increasingly structured by the polar head groups of the surfactant and the counter ions as $W_o$ decreases; for $W_o > 10$ the core has a water pool which increases with size approaching the properties of bulk water. The size of the water core can also be related to the ability to pick-up (i.e., solvate or encapsulate) specific compounds. Thus, important solvent characteristics change as well as the phase boundary in the phase diagram.

The basis of this aspect of invention is the production of reverse micelles in near-critical and supercritical fluids and the utilization of the pressure (or possibly temperature since density is a more fundamental property) variability of the phase boundary and to conduct separations of chemical or biochemical compounds (e.g., proteins, enzymes, etc.). There is also the likelihood that small biological entities suitable for the pressure and temperature of these systems can be suspended in reverse micelles or microemulsions. This makes it possible to utilize the unique fluid properties and to manipulate the conditions of the system to effect a transition from a one-phase to two-phase system (or the reverse) as a key step in a separation scheme. This process can utilize the selective uptake of biological components into the RM phase, and phase separation in a different compartment (where density and $W_o$ would be different). One broad class of separation processes uses the RM phase to transport the hydrophilic substance from one region to another in a separation process. In this case, pressure is used to determine what can be dissolved in the RM and transported, but pressure is held constant. The RM can be used to transport substances between different vessels, or regions. This process can be executed in tandem with chemical reaction processing to modify the product.

The nature of the ternary phase diagrams for the water-AOT-propane system is such as to offer a wide range of options for designing separation processes. The crucial point is that the variability of the phase boundary for the water-AOT-propane ternary system (or pseudo ternary system when the actual components being processed are introduced) provides the basis for these separations. Ternary phase diagrams for liquid propane at 25° C. and supercritical propane at 103° C. in FIG. 2 illustrate the effects of pressure and temperature. Also given are phase diagrams for ethane and iso-octane (a conventional widely studied liquid system). It can be seen that behavior for the propane diagrams are dramatically different; the effect of pressure is greater and $W_o$ varies over the crucial 5-30 $W_o$ range at moderate pressures. Again, the important step in this process is uptake of the component(s) being separated by the RM phase. Many processes of interest also involve the subsequent transfer into a liquid aqueous phase from the reverse micelle. Separation occurs by changing the solvent character of the reverse micelles (which can include actually manipulating the mixture composition, i.e., adding more water, changing ionic strength, pH, etc.) in conjunction with a change in the phase behavior of the system. This may involve flow of the reverse micelle phase into a separate compartment (where pressure is also adjusted and possibly water added).

Surfactants

The anionic surfactant AOT is an excellent reverse micelle surfactant in part because of the favorable packing geometry of the surfactant molecule in the interfacial area. AOT readily forms reverse micelle and microemulsions in near critical and supercritical fluids such as ethane and propane. Other types of surfactants such as cationic, nonionic and zwitterionic surfactants have also been used successfully to form microemulsions in near critical and supercritical fluids.

A cationic surfactant didodecyl dimethyl ammonium bromide, (DDAB), has been used in the propane water system. This system exhibits both a maximum and a minimum in its capacity to solubilized water. The surfactant is insoluble in either pure fluid or pure water, but at a high enough water content the interfacial curvature between the polar and nonpolar phase becomes favorable for microemulsion formation. This effect explains why a minimum water-to-surfactant ratio is required for microemulsion formation.

A class of nonionic surfactants, the polyoxyethylene ethers (e.g., Brij 30, Brij 52) forms reverse micelle-type microemulsions in near critical and supercritical fluids. To maximize the water solubilizing capacity of these surfactants in fluid, it is important that the surfactant have the proper balance of hydrophobic and hydrophilic components.

A zwitterionic surfactant, lecithin, forms a reverse micelle phase in near critical and supercritical propane which can readily dissolve appreciable amounts of water and even large hydrophilic proteins such as Cytochrome-C. This is not intended to be an exhaustive list of surfactants which form reverse micelle or microemulsion phases in near critical and supercritical fluids but rather shows the diversity of substances which can form these structures.

Having described and illustrated the principles of our invention and preferred embodiments in several examples, it should be apparent to those skilled in the art that the invention may be modified in arrangement and detail without departing from such principles. We claim all modifications coming within the scope and spirit of the following claims.

REFERENCES

1. Neogi, P. *In Microemulsions: Structure and Dynamics;* Friberg, S. E.; Bothorel, P. Eds.; CRC Press: Boca Raton, 1987, pp. 197-210.
2. Langevin; D. *In Reverse Micelles;* Luisi, P. L., Straub, B. E., Eds.; Plenum Press: New York, 1984; pp. 287-303.
3. Luisi, P. L., "Angew. Chem. Int. Engl.," 1985, 24, 439-450.
4. Goklen, K. E.; Hatton, T. A. In *Separation Science and Technology;* Bell, J. T.; Watso, J. S., Eds.; Marcel Dekker: New York, 1987, pp. 831-841.
5. Leong, Y. S.; Candau, F., "J. of Phys. Chem.," 1982, 86, 2269-2271.
6. Luisi, P. L., Meier, P., Imre, V. E., Pande, A. In *Reverse Micelles;* Luisi, P. L.; Straub, B. E., Eds.; Plenum Press: New York, 1984; pp. 323-337.
7. Hernandez-Torres, M. A.; Landy, J. S.; Dorsey, J. G., "Anal. Chem.," 1986, 58, 744-747.
8. Goklen, K. E.; Hatton, T. A.; "Biotechnol. Prog.," 1985, 1, 69-74.
9. Eicke, H. F.; Kubik, R.; Hasse, R.; Zschokke, I. In *Surfactants in Solution;* Mittal, K. L.; Lindman, B.; Eds.; Plenum Press: New York, 1984, pp. 1533-1549.
10. Zulauf, M.; Eicke, H. F., "J. Phys. Chem.," 1979, 83, 480-486.
11. Kotlarchyk, M.; Huang, J. S.; Chen, S. H., "J. Phys. Chem.," 1985, 89, 4382-4386.

12. Smith, R. D.; Udseth, H. R.; Wright, B. W. In *Supercritical Fluid Technology;* Penninger, J. M. L.; Radosz, M.; McHugh, M. A.; Krukonis, V. J., Eds.; Elsevier: Amsterdam, 1985, pp. 191-223.
13. *Chemical Engineering at Supercritical Fluid Conditions;* Paulaitis, M. E., Penninger, J. M. L., Gray, R. D., Davidson, P., Eds.; Ann Arbor Science: Ann Arbor, 1983.
14. Wong, J. M.; Johnston, K. P., "Biotechnol. Prog.," 1986, 2, 29-39.
15. Yonker, C. R.; Frye, S. L.; Kalkwarf, D. R.; Smith, R. D., "J. Phys. Chem.," 1986, 90, 3022-3026.
16. Kotlarchyk, M.; Chen, S.; Huang, J. S.; Kim, M. W., "Physical Review A.," 1984, 29, 2054-2069.
17. Prausnitz, J. M. *Molecular Thermodynamics of Fluid-Phase Equilibria:* Prentice-Hall: New Jersey, 1969.
18. Schneider, G. M. Angew. Chem. Int. Ed. Engl. 1978, 17, 716-727.
19. Eckert, C. A.; Ziger, D. H.; Johnston, K. P.; Kim, S., "J. Phys. Chem.," 1986, 90, 2738-2746.
20. Evans, D. F.; Mitchell, D. J.; Ninham, B. W., "J. Phys. Chem.," 1986, 90, 2817-2825.
21. Jonsson, B; Wennerstrom, H., "J. Phys. Chem.," 1987, 91, 338-352.
22. Mitchell, D. J.; Ninham, B. W., "J. Chem. Soc. Faraday Trans. 2," 1981, 77, 601-629.
23. Nagy, J. B.; Gourgue, A; DeRouane, E. G., *Preparation of Catalysts III,* 1983, pp. 193-202.
24. El Seoud, O. A., Chinelatto, A. M., Shimizu, M. R., J. Colloid Interface Sci. 1982, 88, 420-427.
25. *Surfactants in Solution;* Mittal, K. L., Lindman, B., Eds.; Plenum Press: New York, 1984; Vol. 3.
26. Wennerstrom, H; Lindman, B., "Phys. Rep.," 1979, 52, 1-86.
27. Frank, S. G., Zografi, G. J., "Colloid Interface Sci.," 1969, 29, 27-35.
28. Assih, T., Delord, P., Larche, F. C. In *Surfactants in Solution* Mittal, K. L., Lindman, B., Eds; Plenum Press: New York, 1984; Vol. 3, pp. 1821-1828.
29. Nicholson, J. D., Clarke, J. H. R. In *Surfactants in Solution,* Mittal, K. L., Lindman, B., Eds., Plenum Press: New York, 1984; Vol. 3, pp. 1663-1674.
30. Delord, P., Larche, F. C. *In Reverse Micelles,* Luisi, P. L., Straub, B. E., Eds; Plenum Press: New York, 1984; pp. 137-141.
31. Rizzo, V. J., "Colloid Interface Sci.," 1986 110, 110-113.
32. Pileni, M. P.; Zemb, T; Petit, C., "Chem. Phys. Lett.," 1985, 118, 414-420.
33. Ramesh, V.; Labes, M. M., "J. Am. Chem. Soc.," 1986, 108, 4643-4644.
34. Leser, M. E; Wei, G.; Luisi, P. L.; Maestro, M., "Biochem. Biophys. Acta," 1986, 235, 629-635.
35. Arunyanart, M; Cline Love, L. J., "Anal. Chem. 1985, 57, 2836-2843.
36. Arunyanart, M.; Cline Love, L. J., "Anal. Chem.," 1984, 56, 1557-1561.
37. Cline Love, L. J; Habarta, J. G; Dorsey, J. G. "Anal. Chem., 1984, 56, 1132A-1148A.
38. Pelizetti, E; Pramauro, E., "Anal. Chim. Acta," 1985, 169, 1-29.
39. Szepesy, L; Combellas, C.; Caude, M.; Rosset, R., "J. Chromatogr.," 1982, 237, 65-78.
40. Souteyrand, C.; Caude, M; Rosset, R., "J. Chromatogr.," 1983, 262, 1-18.
41. Souteyrand, C.; Caude, M.; Rosset, R., "J. Chromatogr," 1984, 316, 373-388.
42. Landy, J. S; Dorsey, J. G., "J. Chromatogr. Sci.," 1984, 22, 68-70.
43. Dorsey, J. G.; Khaledi, M. G.; Landy, J. S.; Lin, J.-L., "J. Chromatogr.," 1984, 316, 183-191.
44. DeLuccia, F.; Arunyanart, M; Cline Love, L. J., "Anal. Chem.," 1985, 57, 1564-1568.
45. Arunyanart, M; Cline Love, L. J., "J. Chromatogr. Biomed. Appl.," 1985, 342, 293-301.
46. Risby, T. H.; Jiang, L., "Anal. Chem.," 1987, 59, 200-202.
47. Foley, J. P.; May, W. E., "Anal. Chem.," 1987, 59, 102-109.
48. Foley, J. P.; May, W. E., "Anal. Chem.," 1987, 59, 110-115.
49. Lauer, H. H.; McManigill, D.; Board, R. D., "Anal. Chem.," 1983, 55, 1370-1375.
50. Wright, B. W; Kalinoski, H. T.; Smith, R. D., "Anal. Chem.," 1985, 57, 2823-2829.
51. Tang, M.; Deming, S. N., "Anal. Chem.," 1983, 55, 425-428.
52. Balchunas, A. T.; Capacci, M. J.; Sepaniak, M. J.; Maskarinec, M. P., "J. Chromatogr. Sci.," 1985, 23, 381-384.
53. Magid, L. J.; Kon-no, K.; Martin, C. A., "J. Am. Chem. Soc.," 1981, 85, 1434-1439.
54. Kasturi, A.,; Gilpin, R. K., "J. Chromatogr. Sci.," 1987, 25, 29-32.
55. Bidlingmeyer, B. A.; Warren, F. V., "Anal. Chem." 1984, 56, 1583A-1596A.
56. Springston, S. R.; Novotny, M., "Anal. Chem.," 1984, 56, 1762-1766.

We claim:

1. A method of separating solute material from a polar fluid in a first polar fluid phase, comprising:

combining a polar fluid, a second fluid that is a gas at standard temperature and pressure and has a critical density, and a surfactant, said solute material is dissolved in the polar fluid to define the first polar fluid phase;

maintaining the combined polar and second fluid surfactant, and solute material dissolved in said polar fluid, under near critical or supercritical temperature and pressure conditions such that the density of the second fluid exceeds the critical density thereof so as to form a reverse micelle system defining a reverse micelle solvent comprising a continuous phase in said second fluid and a plurality of reverse micelles dispersed in the continuous phase; the solute material dissolved in said polar fluid is transported to said reverse micelles;

the first polar fluid phase and the continuous phase are immiscible;

the reverse micelles each comprising a dynamic aggregate of surfactant molecules surrounding a core of the polar fluid and the reverse micelle solvent having a polar fluid-to-surfactant molar ratio W, which can vary over a range having a maximum ratio $W_o$ that determines the maximum size of the reverse micelles;

varying the maximum ratio $W_o$ of the reverse micelle solvent; and transporting said solute material from the first polar fluid phase into the reverse micelles in the continuous phase at an extraction efficiency determined by said near critical or supercritical conditions.

2. A method according to claim 1 wherein the ratio $W_o$ is controlled by varying the density in said reverse micelle system.

3. A method according to claim 1 including varying the polar fluid-to-surfactant ratio W of said reverse micelle phase and thereby separating said solute material from the reverse micelles.

4. A method according to claim 3 wherein the reverse micelle system is a single phase system and said solute material is separated from the reverse micelles by precipitation.

5. A method according to claim 3 wherein the reverse micelle system is removed from the polar fluid phase and said solute material is recovered from the reverse micelles by varying said near critical or supercritical conditions of the reverse micelle solvent.

6. A method according to claim 5 in which the reverse micelle system is removed as a single-phase system and said solute is recovered from the reverse micelle solvent by precipitation.

7. A method according to claim 3 wherein the reverse micelle solvent is removed as a single phase and transferred to a two phase system including a second polar fluid phase, and said solute material is recovered from the reverse micelles by transferring the solute material from the reverse micelle phase to the second polar fluid phase.

8. A method according to claim 1 wherein $W = W_o$, for a two-phase system, and micelle size is increased by increasing $W_o$ to transport solute material into the reverse micelles.

9. A method according to claim 8, wherein $W_o$ is increased by increasing the pressure in said reverse micelle system.

10. A method according to claim 1 wherein said polar fluid is water and said solute material is a biological or biochemical compound.

11. A method according to claim 10 wherein said biological or biochemical compound comprises a protein compound.

12. A method according to claim 10 wherein $W_o$ is controlled by varying pressure in said reverse micelle system.

13. A method according to claim 10 wherein said second fluid is propane.

14. A method according to claim 1 including removing at least a portion of said reverse micelle solution from said polar fluid phase and reducing $W_o$ in the removed portion to recover the solute material from the reverse micelles.

15. A method according to claim 14 wherein $W_o$ is reduced by varying one of temperature, pressure and composition of the reverse micelle phase.

16. A method according to claim 1 wherein said solute material includes one of hemoglobin, myoglobin and cytochrome-C.

17. A method according to claim 1, wherein the first polar fluid phase includes a solid material, with the solute material incorporated therein, immersed in the reverse micelle phase.

18. A method according to claim 1 wherein the solute material comprises one of a highly polar compound and a thermally labile compound.

19. A method according to claim 1 wherein the first polar phase includes at least two solutes, including controlling pressure so as to make the reverse micelle solvent selective for one of the solutes.

20. A method according to claim 19, wherein the solutes are biochemical compounds.

21. A method according to claim 19, wherein the solutes are proteins.

22. A method of fluid chromatographic separation of solute components from a solute composition, comprising:
 introducing a polar fluid, a second fluid that is a gas at standard temperature and pressure and has a critical density, a surfactant and said solute composition; respectively, into a chromatographic column;
 maintaining the combined polar and second fluids, surfactant and solute composition under a pressure and temperature such that the density of the second fluid exceeds the critical density thereof so as to form a near critical or supercritical reverse micelle system having a continuous phase defined in said second fluid and a plurality of reverse micelles dispersed in the second continuous phase;
 the reverse micelles each comprising a dynamic aggregate of surfactant molecules surrounding a core of the polar fluid and collectively having a polar fluid-to-surfactant ration $W_o$, which can vary over a range having a maximum ratio $W_o$ that determines the maximum size of the reverse micelles;
 forming an enhanced mobile phase including said near critical or supercritical reverse micelle phase capable of solvating solute constituents from said solute composition in said chromatographic column; and
 separating said solute constituents from said solute composition in the mobile phase.

23. A method according to claim 22 wherein said separating step is controlled by varying the polar fluid-to-surfactant ratio W of the mobile phase.

24. A method according to claim 23 wherein the ratio W is increased over a range up to a maximum $W_o$ by adding polar fluid during separation.

25. A method according to claim 22 wherein said separating step is controlled by varying the number of micelles in said mobile phase while maintaining the polar fluid-to-surfactant ratio W at a constant level.

26. A method according to claim 25 wherein said number of micelles is increased by increasing the amounts of polar fluid and surfactant in the mobile phase.

27. A method according to claim 22 including changing reverse micellar composition of the mobile phase during separation.

28. A method according to claim 22 including changing density or pressure and maintaining a constant reverse micellar composition of the mobile phase during separation.

29. A method of separating solute material from a solid material, comprising:
 combining said solute material and solid material with a first polar fluid and a second fluid that is a gas at standard temperature and pressure and has a critical density, and a surfactant;
 maintaining the combined solute material, solid material, first polar fluid, second fluid, and surfactant, under near critical or supercritical temperature and pressure conditions such that the density of the fluid exceeds the critical density thereof, so as to form a reverse micelle system defining a reverse micelle solvent including a continuous phase, including the solute material and solid material, and a plurality of reverse micelles dispersed in the continuous phase;
 the reverse micelles comprising a dynamic aggregate of surfactant molecules surrounding a core of the polar fluid, and the reverse micelle solvent having a polar fluid-to-surfactant molar ratio W, which can vary over a range having a maximum ratio $W_o$ that determines the maximum size of the reverse micelles;

varying the maximum ratio $W_o$ of the reverse micelle solvent; and transporting said solute material from said solid material into the reverse micelles at an extraction efficiency determined by said near critical or supercritical conditions.

30. A method of separating solute material from a solid material, comprising:

combining said solute material and solid material with a fluid that is a gas at standard temperature and pressure and has a critical density, and a surfactant;

maintaining the combined solute material, solid material, fluid, and surfactant, under near critical or supercritical temperature and pressure conditions such that the density of the fluid exceeds the critical density thereof, so as to form a reverse micelle system defining a reverse micelle solvent including a continuous phase, including the solute material and solid material, and a plurality of reverse micelles dispersed in the continuous phase;

the reverse micelles comprising a dynamic aggregate of surfactant molecules with polar head groups of the surfactant comprising the core of the reverse micelles; and transporting said solute material from said continuous phase into the reverse micelles at an extraction efficiency determined by said near critical or supercritical conditions.

* * * * *